(12) United States Patent
Suzuki et al.

(10) Patent No.: US 10,780,237 B2
(45) Date of Patent: Sep. 22, 2020

(54) ATOMIZING UNIT

(71) Applicant: JAPAN TOBACCO INC., Tokyo (JP)

(72) Inventors: Akihiko Suzuki, Tokyo (JP); Manabu Takeuchi, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 383 days.

(21) Appl. No.: 15/851,064

(22) Filed: Dec. 21, 2017

(65) Prior Publication Data

US 2018/0110940 A1 Apr. 26, 2018

Related U.S. Application Data

(63) Continuation of application No. PCT/JP2016/068930, filed on Jun. 24, 2016.

(30) Foreign Application Priority Data

Jun. 26, 2015 (WO) .................. PCT/JP2015/068578

(51) Int. Cl.
*A61M 11/04* (2006.01)
*A24F 47/00* (2020.01)
*A61M 15/06* (2006.01)

(52) U.S. Cl.
CPC .......... *A61M 11/042* (2014.02); *A24F 47/00* (2013.01); *A24F 47/008* (2013.01); *A61M 11/041* (2013.01); *A61M 15/06* (2013.01); *A61M 2205/27* (2013.01); *A61M 2205/8206* (2013.01)

(58) Field of Classification Search
CPC ..... A61M 11/042; A61M 15/06; A24F 47/00; A24F 47/008
See application file for complete search history.

(56) References Cited

U.S. PATENT DOCUMENTS

| 8,678,012 B2 | 3/2014 | Li et al. |
| 8,689,805 B2 | 4/2014 | Hon |
| 9,320,300 B2 | 4/2016 | Hon |
| 2014/0130796 A1 | 5/2014 | Liu |
| 2015/0090280 A1 | 4/2015 | Chen |

(Continued)

FOREIGN PATENT DOCUMENTS

| CN | 201830900 U | 5/2011 |
| CN | 103974639 A | 8/2014 |

(Continued)

OTHER PUBLICATIONS

Taiwanese Office Action and Search Report for Taiwanese Application No. 105120147, dated Feb. 22, 2018, with an English translation of the Office Action.

(Continued)

*Primary Examiner* — Timothy A Stanis
*Assistant Examiner* — Cana A Gallegos
(74) *Attorney, Agent, or Firm* — Birch, Stewart, Kolasch & Birch, LLP

(57) ABSTRACT

This atomization unit is provided with a reservoir that holds an aerosol source, an atomization part that atomizes the aerosol source, and a cap body that blocks a supply port for supplying the aerosol source to the reservoir, wherein movement of the cap body away from the reservoir causes the atomization part and/or a power supply member, which electrically connects a power source and the atomization part, to break.

15 Claims, 19 Drawing Sheets

(56) References Cited

U.S. PATENT DOCUMENTS

2015/0173422 A1 6/2015 Liu
2015/0181937 A1 7/2015 Dubief et al.

FOREIGN PATENT DOCUMENTS

| | | |
|---|---|---|
| CN | 203913378 U | 11/2014 |
| CN | 204070546 U | 1/2015 |
| CN | 104621718 A | 5/2015 |
| JP | 3164992 U | 12/2010 |
| JP | 2012-517229 A | 8/2012 |
| JP | 2015-504652 A | 2/2015 |
| TW | 201334713 A1 | 9/2013 |

OTHER PUBLICATIONS

International Search Report (PCT/ISA/210) issued in PCT/JP2016/068930, dated Aug. 30, 2016.
Japanese Office Action for Japanese Application No. 2017-525468, dated Sep. 4, 2018, with English translation.

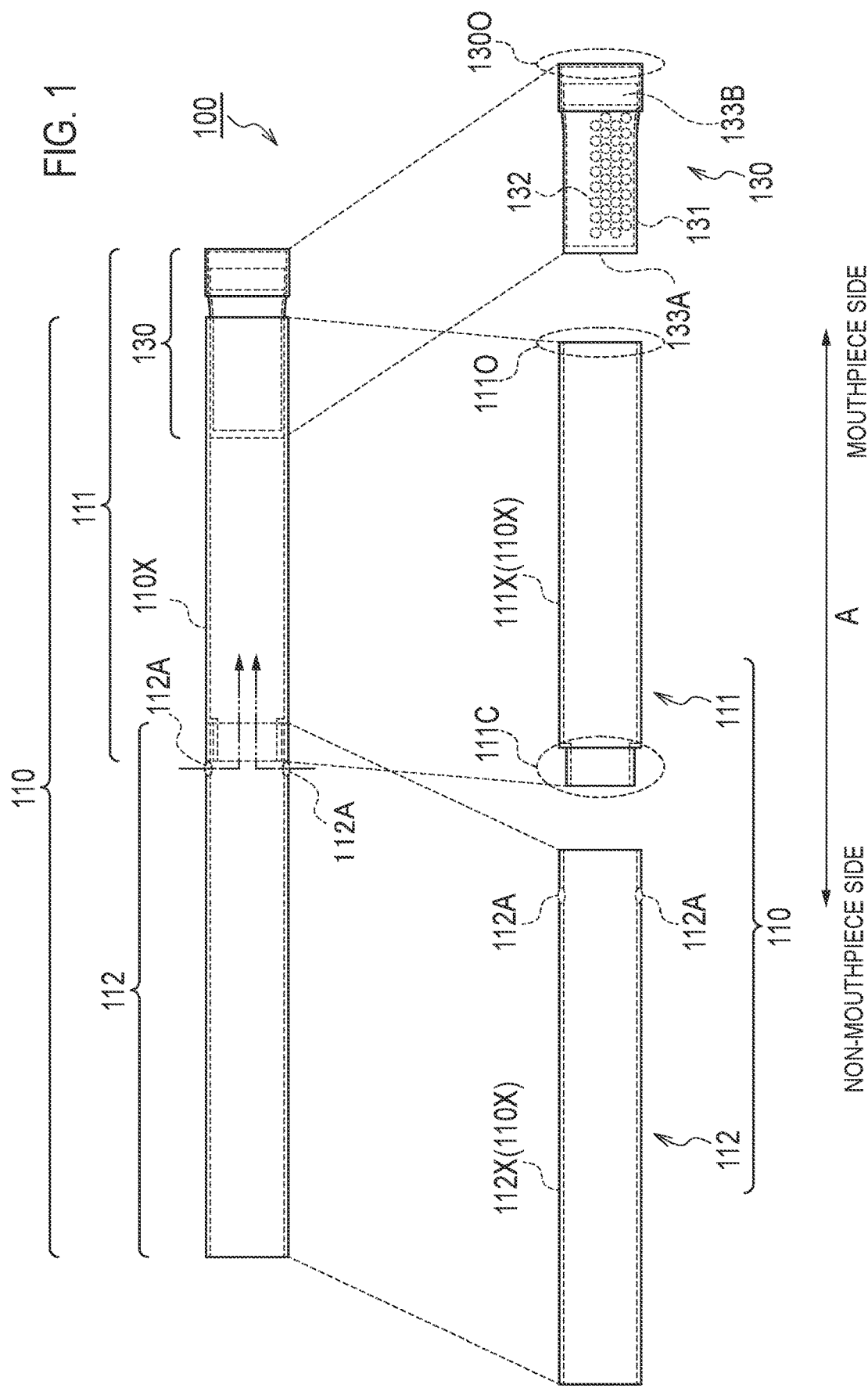

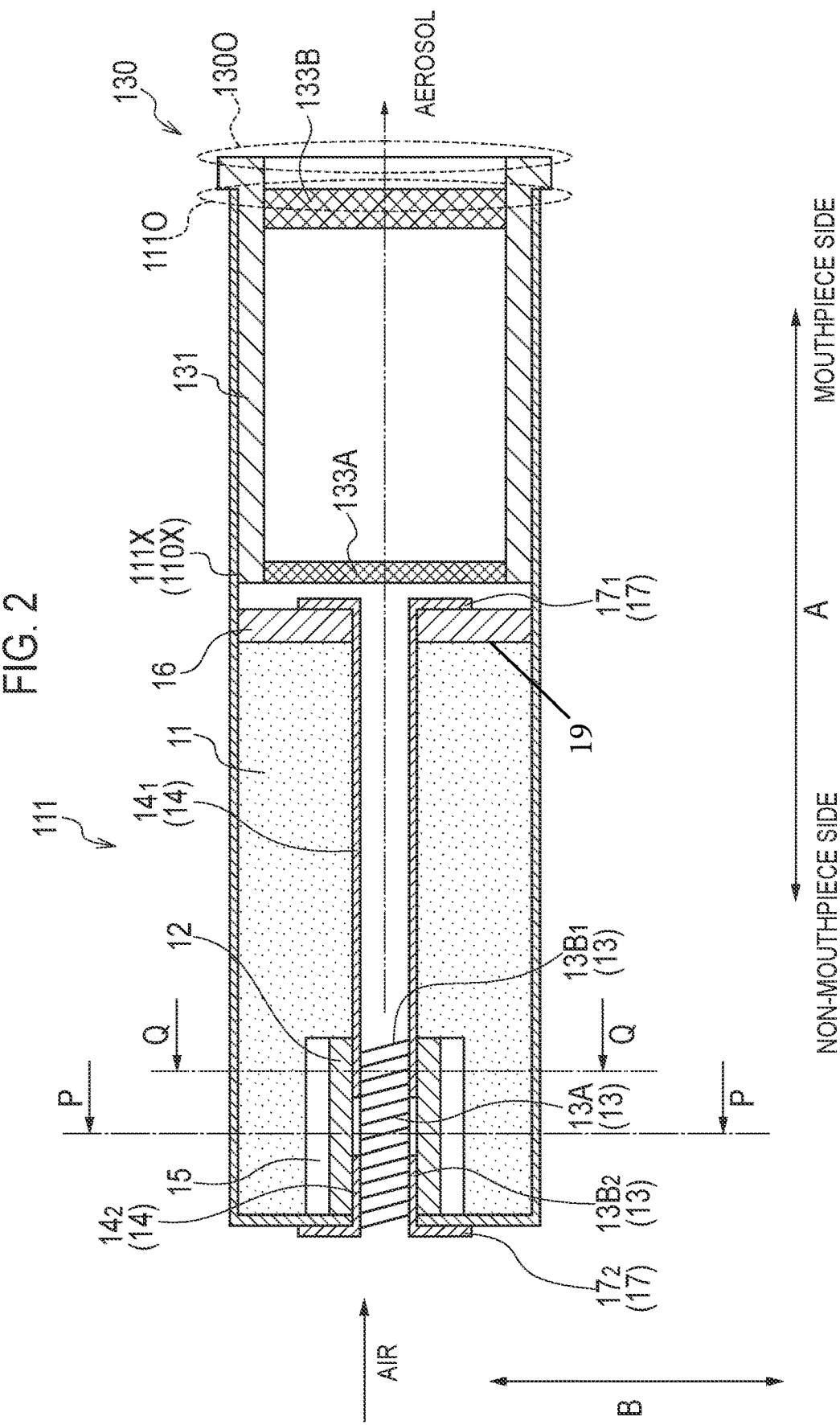

ATOMIZING UNIT

TECHNICAL FIELD

The present invention relates to an atomizing unit having an atomizing portion for atomizing an aerosol source without burning.

BACKGROUND ART

Conventionally, a non-burning type flavor inhaler for inhaling flavor without burning is known. The non-burning type flavor inhaler comprises an atomizing unit for atomizing an aerosol source without burning. The atomizing unit includes a reservoir for storing an aerosol source, a liquid holding member for holding an aerosol source supplied from the reservoir, and an atomizing portion for atomizing the aerosol source held by the liquid holding member. The liquid holding member has a shape extending along a predetermined direction, and is disposed to contact the outer side surface of the atomizer in a direction orthogonal to the predetermined direction (for example, Patent Literatures 1 and 2).

CITATION LIST

Patent Literature

Patent Literature 1: PCT National Publication No. 2012-517229
Patent Literature 2: PCT National Publication No. 2015-504652

SUMMARY OF THE INVENTION

A first feature is summarized as an atomizing unit comprising: a reservoir configured to store an aerosol source; an atomizing portion configured to atomize the aerosol source; and a cap configured to cover a supply port for supplying the aerosol source to the reservoir, wherein at least one of the atomizing portion and a power supply member electrically connected to a power source and the atomizing portion is broken by a movement of separating the cap from the reservoir.

A second feature according to the first feature is summarized as that the supply port is provided on the opposite side of a connection part to the power source with respect to the reservoir.

A third feature according to the first feature or the second feature is summarized as that the part connecting the power source, the reservoir, the cap and the mouthpiece side opening are arranged side by side in this order in a predetermined direction in which aerosol atomized by the atomizing portion is directed toward the mouthpiece-side opening.

A fourth feature according to the third feature is summarized as that the connection part to the power source, the reservoir, the cap, and the mouthpiece side opening are arranged on a straight line.

A fifth feature according to any one of the first to fourth features is summarized as that the supply port is open toward a predetermined direction in which the aerosol atomized by the atomizing portion is directed toward the mouthpiece side opening, and the cap is disposed to cover the supply port from the mouthpiece side opening.

A sixth feature according to any one of the first to fifth features is summarized as that the supply port is provided at an end of the reservoir on a downstream side of an air flow path.

A seventh feature according to any one of the first to sixth features is summarized as that the atomizing portion is deformed along with a movement of separating the cap from the reservoir.

An eight feature according to any one of the first to seventh features is summarized as that the power supply member is provided in a separating direction of at least a part of the cap, the separating direction being a direction of separating the cap from the reservoir.

A ninth feature according to any one of the first to eighth features is summarized as that the power supply member includes: a first power supply portion including a part extending from the atomizing portion to the connection part to the power source; and a second power supply portion extending from the atomizing portion to the opposite side of the connection part to the power source.

A tenth feature according to any one of the first to ninth features is summarized as that the power supply member is disposed through inside of the cap.

An eleventh feature according to any one of the first to tenth features is summarized as that the power supply member is fixed to the cap.

A twelfth feature according to any one of the first to eleventh features is summarized as the atomizing unit comprising: a cylindrical member having a tubular shape forming at least a part of an air flow path and formed of a conductive member, wherein the power supply member includes the cylindrical member.

A thirteenth feature according to any one of the first to twelfth features is summarized as that the atomizing portion is more likely to break than the power supply member.

A fourteenth feature according to any one of the first to thirteenth features is summarized as that the atomizing portion is a coil having a shape extending along a predetermined direction in which aerosol atomized by the atomizing portion is directed toward the mouthpiece side opening.

A fifteenth feature according to the fourteenth feature is summarized as that an inside of the coil is hollow.

In the features described above, the power supply member may be any member for electrically connects the atomizing portion and the power source. The power supply member may be, for example, a cylindrical member formed of a conductive member, a flange electrically connected to the cylindrical member, or a lead wire connecting the cylindrical member or the flange to to the power source.

In the above features, the atomizing portion may be a resistance heating element that generates heat by a power supply output supplied to the atomizing portion. Further, the atomizing portion is formed of a wire having a spiral shape, and may be a coil having a shape extending along a predetermined direction.

In the above features, the atomizing portion may be configured to atomize the aerosol source by the power supply output supplied to the atomizing portion. For example, the atomizing portion may be configured to atomize the aerosol source by ultrasonic vibration.

BRIEF DESCRIPTION OF THE DRAWINGS

FIG. 1 is a diagram showing a non-burning type flavor inhaler 100 according to an embodiment.
FIG. 2 is a diagram showing an atomizing unit 111 according to an embodiment.

MODE FOR CARRYING OUT THE INVENTION

Figure 3A:
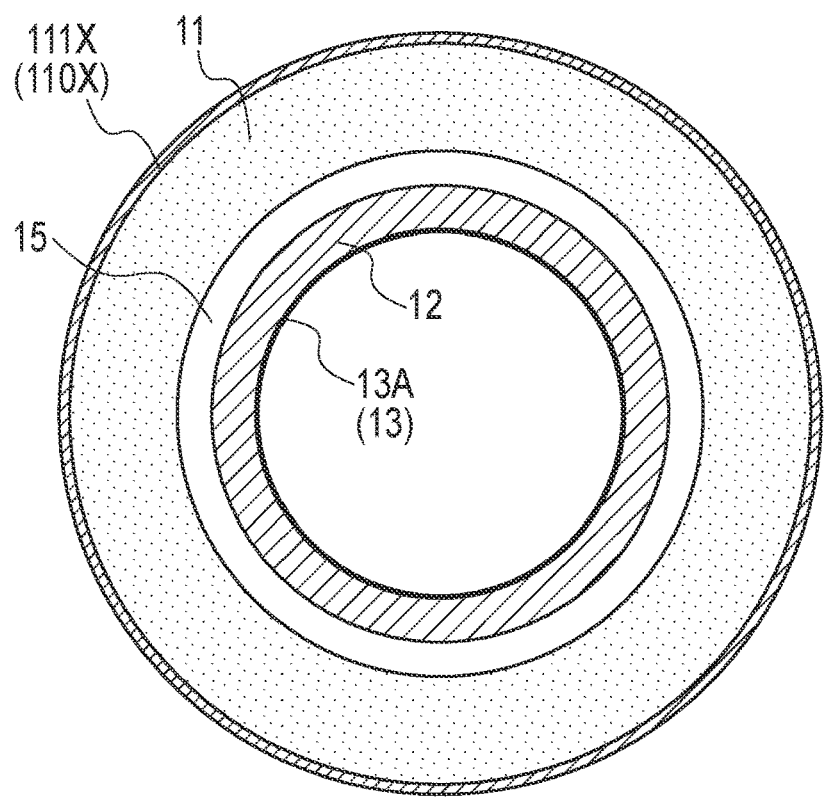
FIG. 3 (A) is a diagram showing a P-P cross-section shown in FIG. 2, and FIG. 3 (B) is a diagram showing a Q-Q cross-section shown in FIG. 2.

Hereinafter, embodiments of the present invention will be described. In the following description of the drawings, the same or similar reference numerals denote the same or similar parts. It should be noted that the drawings are schematic, and the ratios of dimensions and the like may be different from the actual ones.

Therefore, specific dimensions and the like may be determined by referring to the following description. Of course, the drawings may include the parts having different dimensions and ratios.

SUMMARY OF DISCLOSURE

In the atomizing unit described in Background Art, from the viewpoint that the user properly uses the non-burning type flavor inhaler, it is preferable to prevent the use of the non-burning type flavor inhaler accompanied by reinjection of the aerosol source to the reservoir.

An atomizing unit according to a summary of disclosure comprises: a reservoir configured to store an aerosol source; an atomizing portion configured to atomize the aerosol source; and a cap configured to cover a supply port for supplying the aerosol source to the reservoir, wherein at least one of the atomizing portion and a power supply member electrically connected to a power source and the atomizing portion is broken by a movement of separating the cap from the reservoir.

According to the summary of disclosure, at least one of the atomizing portion and the power supply member electrically connecting the power source and the atomizing portion is broken by the movement of separating the cap from the reservoir. Therefore, it is possible to effectively prevent the use of the non-burning type flavor inhaler accompanied by reinjection of the aerosol source to the reservoir.

Embodiment (Non-Burning Type Flavor Inhaler)

Hereinafter, a non-burning type flavor inhaler according to an embodiment will be described. FIG. 1 is a diagram showing a non-burning type flavor inhaler 100 according to an embodiment. The non-burning type flavor inhaler 100 is a device for inhaling an inhaling flavor component without burning, and has a shape extending along a predetermined direction A that is a direction from a non-mouthpiece end to a mouthpiece end. FIG. 2 is a diagram illustrating an atomizing unit 111 according to an embodiment. FIG. 3 (A) is a diagram showing a P-P cross-section of the atomizing unit 111 shown in FIG. 2, and FIG. 3 (B) is a diagram showing a Q-Q cross-section of the atomizing unit 111 shown in FIG. 2. In the following description, it should be noted that the non-burning type flavor inhaler 100 is simply referred to as a flavor inhaler 100.

As shown in FIG. 1, the flavor inhaler 100 includes an inhaler body 110 and a cartridge 130.

The inhaler body 110 constitutes a main body of the flavor inhaler 100, and has a shape capable of connecting the cartridge 130. Specifically, the inhaler body 110 has an inhaler housing 110 X, and the cartridge 130 is connected to a downstream end of the inhaler housing 110 X. The inhaler body 110 includes an atomizing unit 111 for atomizing an aerosol source without burning, and an electrical unit 112. The atomizing unit 111 and the electrical unit 112 are accommodated in the inhaler housing 110 X.

In the embodiment, the atomizing unit 111 includes an atomizing unit housing 111 X constituting a part of the inhaler housing 110X. The atomizing unit 111 includes a connection part 111 C to a power source provided in the electrical unit 112, and a mouthpiece side opening 111 O provided on the opposite side of the connection part 111 C. The connection part 111 C is, for example, a connector to be connected to a power source. The mouthpiece side opening 111 O is an opening for receiving the cartridge 130, and is provided in the mouthpiece end. As shown in FIG. 2, the atomizing unit 111 includes a reservoir 11, a liquid holding member 12, a heating element 13, a cylindrical member 14 (cylindrical member $14_1$ and cylindrical member $14_2$), a cover member 15, a cap 16 and a flange 17 (flange $17_1$ and flange $17_2$). These members are accommodated in the atomizing unit housing 111 X. The atomizing unit housing 111 X has a shape (for example, a cylindrical shape) extending along the predetermined direction A. In FIG. 2, the connection part 111 C is omitted, but the connection part 111 C is provided in the non-mouthpiece end (the electrical unit 112 side) of the flange $17_2$.

The reservoir 11 stores an aerosol source. The reservoir 11 has a configuration (size, material, structure, etc.) suitable for storing an aerosol source used for a plurality of puff actions. For example, the reservoir 11 may be a porous body formed of a material such as a resin web and the like, or a cavity for storing an aerosol source. The reservoir 11 is preferably able to store more aerosol sources per unit volume. The reservoir 11 may be disposed at a position where the aerosol source can be supplied to the liquid holding member 12, and contacts at least a part of the liquid holding member 12. In the embodiment, as shown in FIGS. 3 (A) and 3 (B), at least a part of the reservoir 11 is preferably arranged outside the cover member 15 in a direction B orthogonal to the predetermined direction A.

The liquid holding member 12 holds the aerosol source supplied from the reservoir 11. The liquid holding member 12 has a configuration (size, material, structure, etc.) suitable for holding a part of the aerosol source storable in the reservoir 11 (for example, an aerosol source used for one puff action) by transferring from the reservoir 11 to a position contacting or close to the heating element 13. The liquid holding member 12 may be a member for transferring the aerosol source from the reservoir 11 to the liquid holding member 12 by capillary phenomenon. The liquid holding member 12 transfers the aerosol source to the liquid holding member 12 by contacting the reservoir 11. When the reservoir 11 is a hollow, the contact between the liquid holding member 12 and the reservoir 11 means that the liquid holding member 12 is exposed to the cavity (reservoir 11). However, it should be noted that after the aerosol source is filled in the reservoir 11, the liquid holding member 12 is arranged to contact the aerosol source filled in the cavity (reservoir 11). For example, the liquid holding member 12 is made of glass fiber or porous ceramic. For example, the liquid holding member 12 is a wick made of glass fiber or porous ceramic. The liquid holding member 12 preferably has a heat resistance to withstand heating of the heating element 13. As shown in FIGS. 3 (A) and 3 (B), the liquid holding member 12 has a cylindrical shape extending along the predetermined direction A.

Here, at least a part of the inner side surface of the liquid holding member 12 contacts or comes close to the heating element 13 in the orthogonal direction B. The "at least a part of the inner side surface of the liquid holding member 12 contacts or comes close to the heating element 13" means that the distance between the heating element 13 and the inner side surface of the liquid holding member 12 is maintained to keep the distance between the heating element 13 and the aerosol source to a degree that the aerosol source can be atomized by the heating element 13 when the liquid holding member 12 holds the aerosol source. The distance between the heating element 13 and the inner side surface of the liquid holding member 12 depends on types of the aerosol source and the liquid holding member 12, temperatures of the heating element, and the likes, and may be, for example, 3 mm or less, preferably 1 mm or less. Further, "at least a part of the inner side surface of the liquid holding member 12 contacts with or comes close to the heating element 13" means that the distance between the heating element 13 and the inner side surface of the liquid holding member 12 is kept at a degree that the aerosol source can be atomized by the heating element 13. Thus, when the aerosol source is in a state where atomization of the aerosol source by the heating element 13 is impossible or atomization of the aerosol source is inhibited due to intervention of something between the heating element 13 and the aerosol source, it is not said that at least a part of the inner side surface of the liquid holding member 12 comes close to the heating element 13.

In the embodiment, the inner side surface of the liquid holding member 12 contacts or comes close to the heating portion 13 A of the heating element 13 as shown in FIG. 3 (A). On the other hand, as shown in FIG. 3 (B), a cylindrical member $14_1$ is interposed between the liquid holding member 12 and the first end portion $13 B_1$, and the inner side surface of the liquid holding member 12 does not contact or come close to the first end portion $13 B_1$ of the heating element 13. Similarly, a cylindrical member $14_2$ is interposed between the liquid holding member 12 and the second end portion $13 B_2$, and the inner side surface of the liquid holding member 12 does not contact or come close to the second end portion $13 B_2$ of the heating element 13.

At least a part of the outer side surface of the liquid holding member 12 in the orthogonal direction B is covered with the cover member 15 as shown in FIGS. 3 (A) and 3 (B).

The heating element 13 is an example of an atomizing portion for atomizing the aerosol source held by the liquid holding member 12. In the embodiment, the heating element 13 is a resistance heating element that generates heat by a supplied to the heating element 13. Further, the heating element 13 is formed of a wire having a spiral shape, and is a coil having a shape extending along the predetermined direction A. Further, the inside of the heating element 13 forms at least a part of an air flow path that is a flow path of air inhaled from the mouthpiece end (the outlet 130 O shown in FIG. 1). Preferably, the inside of the heating element 13 is hollow.

Here, the heating element 13 includes the heating portion 13 A, the first end portion $13 B_1$, and the second end portion $13 B_2$. The heating element 13 is provided with a first contact electrically connected to a first pole of the power source and a second contact electrically connected to a second pole of the power source on the wire with a space therebetween. In the embodiment, the first contact is constituted by the first end portion $13 B_1$ and the cylindrical member $14_1$. Similarly, the second contact is constituted by the second end portion $13 B_2$ and the cylindrical member $14_2$.

The heating portion 13 A is formed of a wire between the first contact and the second contact arranged closest to each other on the wire. The first end portion $13 B_1$ is formed of a wire on one side of the heating portion 13 A on the wire (in the embodiment, the wire on the downstream side in the air flow path). The second end portion $13 B_2$ is formed of a wire on the other side of the heating portion 13 A on the wire (in the embodiment, the wire on the upstream side in the air flow path). The pitches of the wires forming the heating portion 13 A, the first end portion $13 B_1$ and the second end portion $13 B_2$ are the same. It is to be noted that the "pitch" means the distance between adjacent wires in the predetermined direction A. The "the pitches of the wires are the same" does not mean that the pitches of the wires are exactly the same, and means that the pitches of the wires are substantially the same. The "substantially the same" means that the difference in the pitches of the wires forming the heating portion 13 A, the first end portion $13 B_1$ and the second end portion $13 B_2$ are not intentionally set, and means that a difference caused by a manufacturing error and the like is acceptable.

The cylindrical member 14 has a tubular shape and includes cylindrical member $14_1$ and a cylindrical member $14_2$. The cylindrical member $14_1$ and the cylindrical member $14_2$ have a tubular shape forming at least a part of an air flow path communicating from an inlet 112 A to an outlet 130 O (mouthpiece end). That is, the cylindrical member $14_1$ constitutes a first cylindrical member, and the cylindrical member $14_2$ constitutes a second cylindrical member spaced from the cylindrical member $14_1$ in the predetermined direction A. It is preferable that each of the cylindrical member $14_1$ and the cylindrical member $14_2$ has a completely closed tubular shape without having an opening on the outer side surface of the cylindrical member $14_1$ and the cylindrical member $14_2$. In the embodiment, the inner diameter of the cylindrical member 14i is the same as the inner diameter of the cylindrical member $14_2$.

The cylindrical member 14 has an aerosol intake to pass aerosol atomized by the heating element 13 to the air flow path. In the embodiment, the cylindrical member 14 includes the cylindrical member $14_1$ and the cylindrical member $14_2$, and the aerosol intake is a space between the cylindrical member $14_1$ and the cylindrical member $14_2$. The heating portion 13 A described above is arranged to be adjacent to the aerosol intake over the entire length of the aerosol intake in the predetermined direction A. The liquid holding member 12 described above is arranged to be adjacent to the aerosol intake over the entire length of the aerosol intake in the predetermined direction A. With such a configuration, the aerosol source held by the liquid holding member 12 can be atomized by efficiently using a portion with good quality other than the end portion of the wire constituting the heating element 13 (coil) as the heating portion 13 A. Incidentally, "adjacent to each other" may be a positional relationship in which the heating portion 13 A (or the liquid holding member 12) is exposed to the aerosol intake, a positional relationship in which a gap exists between the heating portion 13 A (or the liquid holding member 12) and the aerosol intake, or a positional relationship in which a part of the heating portion 13 A (or the liquid holding member 12) enters the aerosol intake. It should be noted that even in an aspect in which the heating portion 13 A (or the liquid holding member 12) is adjacent to the aerosol intake, a positional relationship between the heating portion 13 A and the inner side surface of the liquid holding member 12 satisfies the above-mentioned contact or close relationship.

A part or the whole of the cylindrical member 14 is formed of a conductive member having an electric resistivity lower than that of the wire forming the heating portion 13 A, and constitutes a first contact and a second contact by contacting the heating element 13. The cylindrical member 14 is made of, for example, aluminum or stainless steel (SUS). In the embodiment, the cylindrical member $14_1$ constitutes a first conductive member contacting the first end portion 13 $B_1$ at the first contact, and the cylindrical member $14_2$ constitutes a second conductive member contacting the second end portion 13 $B_2$ at the second contact. The heating portion 13 A described above is exposed from the cylindrical member 14 between the cylindrical member $14_1$ and the cylindrical member $14_2$.

In the embodiment, the cylindrical member $14_1$ is disposed between the liquid holding member 12 and the first end portion 13 $B_1$ in the orthogonal direction B. Likewise, the cylindrical member $14_2$ is disposed between the liquid holding member 12 and the second end portion 13 $B_2$ in the orthogonal direction B.

In the embodiment, as shown in FIG. 3 (B), the cylindrical member 14 constitutes a barrier member having an outer side surface located between the outer side surface of the heating member 13 and the inner side surface of the liquid holding member 12 in the orthogonal direction B. The outer side surface of the cylindrical member 14 is preferably provided at a position facing a part of the inner side surface of the liquid holding member 12. Further, the outer side surface of the cylindrical member 14 is preferably provided at a position facing a part of the inner side surface of the cover member 15. However, the outer side surface of the cylindrical member 14 may be provided at a position not facing the inner side surface of the cover member 15. The cylindrical member 14 preferably has a function of suppressing deformation of the heating element 13 due to a stress in an inward direction of the liquid holding member 12 covered by the cover member 15. That is, the cylindrical member 14 preferably has strength enough to withstand the stress of the cover member 15 pressing the outer side surface of the cylindrical member 14 inwardly in the orthogonal direction B. Therefore, the cylindrical member 14 is preferably formed of a conductive member (for example, stainless steel (SUS)) having a predetermined strength. In the embodiment, since the cylindrical member 14 forming the air flow path has a predetermined strength and the outer side surface of the cylindrical member 14 is provided at a position facing a part of the inner side surface of the cover member 15, deformation of the heating element 13 due to the stress of the cover member 15 and deformation of the air flow path are suppressed.

The cover member 15 restricts the amount of the aerosol source supplied to the liquid holding member 12. As shown in FIGS. 3 (A) and 3 (B), the cover member 15 has a cylindrical shape extending along the predetermined direction A. The cover member 15 is formed of a liquid impermeable member. The cover member 15 may be a liquid impermeable coating. The cover member 15 is preferably formed of a member having a thermal conductivity lower than that of the aerosol source or the liquid holding member 12. With such a configuration, the heat of the heating element 13 is hard to be transmitted to the aerosol source stored in the reservoir 11. The cover member 15 is preferably formed of a member pressing the liquid holding member 12 inwardly, for example, an elastic member. As a member constituting the cover member 15, for example, a silicone resin or a polyolefin resin can be used.

In the embodiment, as shown in FIG. 2, the cover member 15 covers the outer side surface of the liquid holding member 12 over the entire length of the outer side surface of the liquid holding member 12 along the predetermined direction A in a range where the inner side surface of the liquid holding member 12 and the heating element 13 (heating portion 13 A) contact or come close to each other.

Figure 3B:
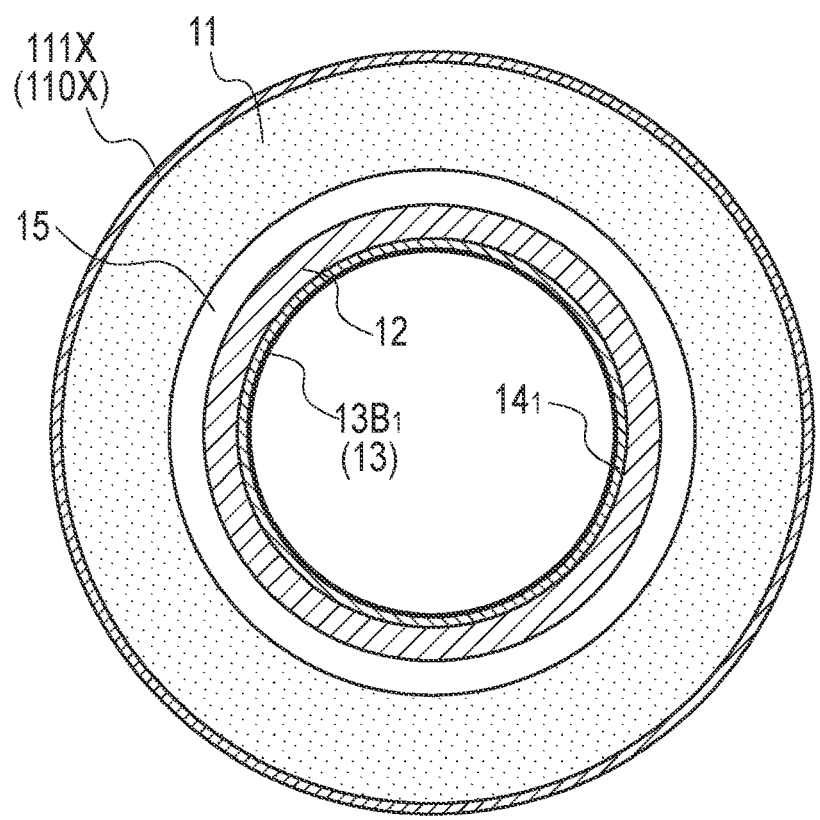
Figure 4A:
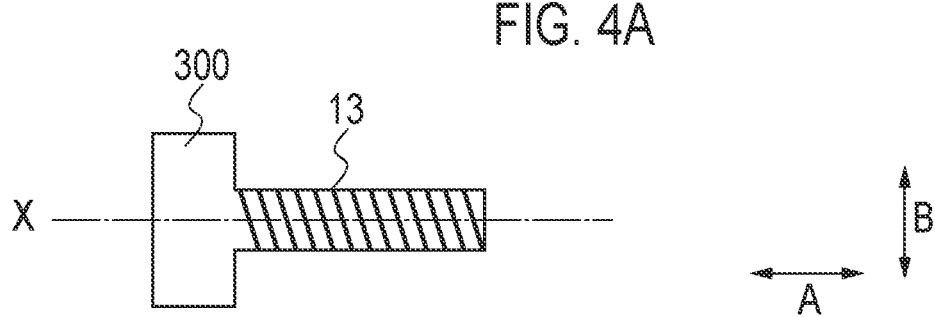
FIGS. 4 (A) to 4 (D) are diagrams for explaining a manufacturing method of an atomizing unit 111 according to an embodiment.
Figure 4B:
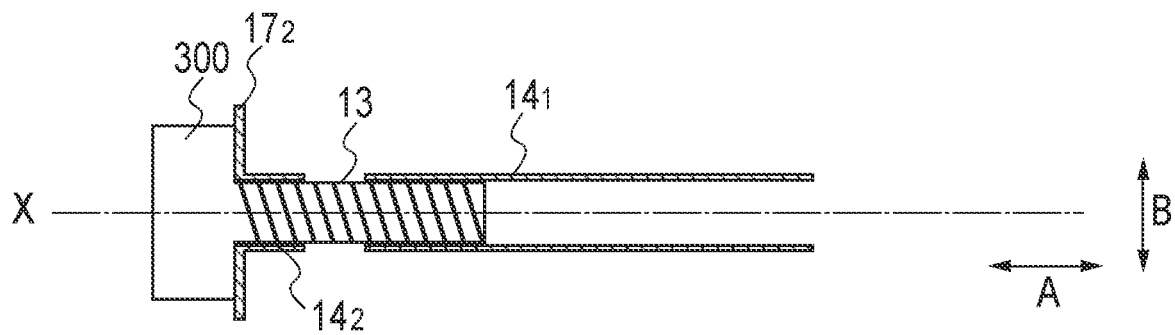
Figure 4C:
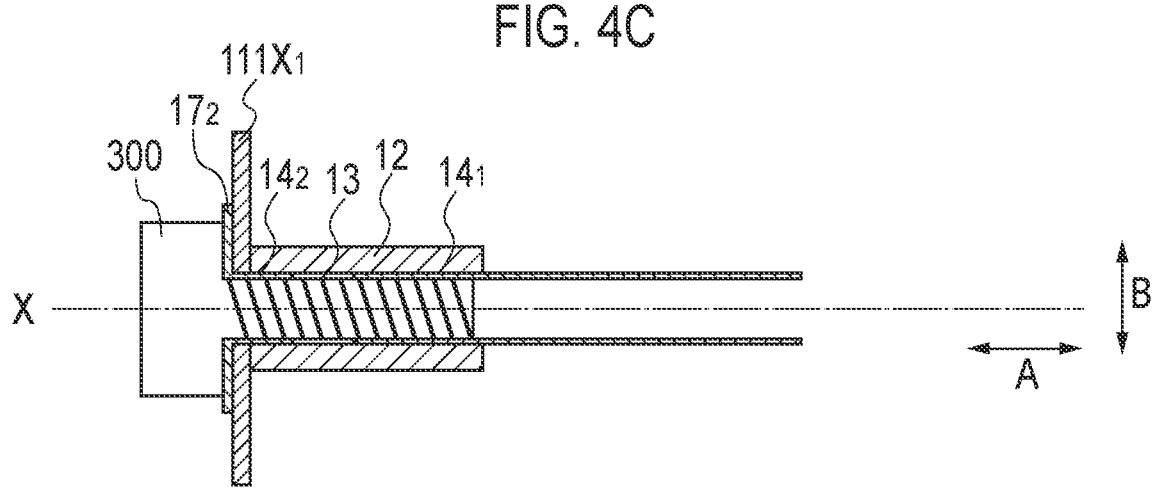
Figure 4D:
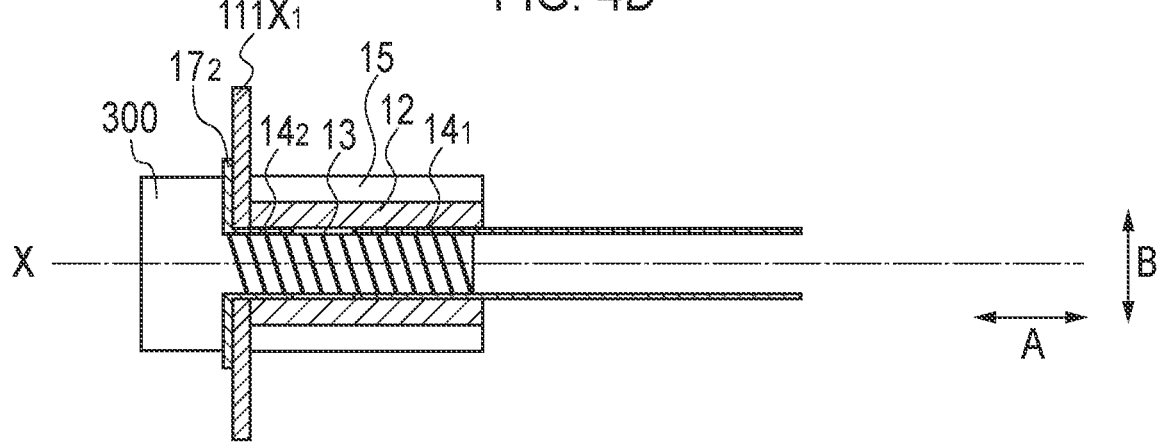

In the embodiment, as shown in FIG. 3(A), the cover member 15 covers the outer side surface of the liquid holding member 12 over the entire circumference of the outer side surface of the liquid holding member 12 in a circumferential direction around the predetermined direction A as an axis in a range where the inner side surface of the liquid holding member 12 and the heating element 13 (heating portion 13 A) contact or come close to each other.

In such a case, preferably, the cover member 15 uniformly covers the outer side surface of the liquid holding member 12. For example, the cover member 15 may have no opening and cover the outer side surface of the liquid holding member 12. Alternatively, the cover member 15 may have ten or more openings, each of which is equally spaced in a predetermined direction (extension direction of the liquid holding member 12) or/in a circumferential direction around the predetermined direction as an axis. Or, the cover member 15 may have a plurality of equally spaced openings as described above, and a covering area, which is an area of the outer side surface of the liquid holding member 12 covered by the cover member 15, may be 60% or more of the area of the outer side surface of the member 12. Or, the cover member 15 may have ten or more equally spaced openings as described above, and the covering area may be 60% or more of the area of the outer side surface of the liquid holding member 12. A range of the outer side surface of the liquid holding member 12 uniformly covered by the cover member 15 may be only a range where the inner side surface of the liquid holding member 12 and the heating element 13 (heating portion 13 A) contact or come close to each other, or may be a whole range where the inner side surface of the cover member 15 and the outer side surface of the liquid holding member 12 contact each other.

As shown in FIGS. 2 and 3 (B), even in a range where the inner side surface of the liquid holding member 12 and the heating element 13 (heating portion 13 A) do not contact or come close to each other, the cover member 15 may cover the outer side surface of the liquid holding member 12.

For example, when the liquid holding member 12 is provided on the whole outside of the heating element 13 (the heating portion 13 A, the first end portion 13 $B_1$, and the second end portion 13 $B_2$), the cover member 15 may cover the outer side surface of the liquid holding member 12 over the entire length of the outer side surface of the liquid holding member 12 along the predetermined direction A in a range where the inner side surface of the cover member 15 and the outer side surface of the holding member 12 contact each other, or may cover the outer side surface of the liquid holding member 12 over the entire circumference of the outer side surface of the liquid holding member 12 in the circumferential direction around the predetermined direction A as an axis.

In the embodiment, it is preferable that the cover member 15 presses the outer side surface of the liquid holding member 12 inwardly in the orthogonal direction B, and brings the inner side surface of the liquid holding member 12 into contact or close to the heating element 13 by a stress of a degree that the heating element 13 is not deformed. Further, in the orthogonal direction B, the thickness of the liquid holding member 12 covered by the cover member 15 is preferably smaller than that of the liquid holding member 12 covered by the cover member 15.

From the viewpoint of applying a stress of a degree that the heating element 13 is not deformed, the cover member 15 preferably covers the outer side surface of the liquid holding member 12 even in a range where the inner side surface of the liquid holding member 12 and the heating element 13 (heating portion 13 A) do not contact or come close to each other. The cylindrical member $14_1$ is preferably provided inside the cover member 15 in a range where the first end portion 13 $B_1$ is provided, and the cylindrical member $14_2$ is preferably provided inside the cover member 15 in a range where the second end portion 13 $B_2$ is provided.

The cap 16 is a member to close a supply port for supplying the aerosol source to the reservoir 11. In the embodiment, the supply port is provided at the end (hereinafter referred to as a downstream end) of the reservoir 11 on the downstream side of the air flow path. In other words, the supply port is provided on the opposite side of the connection part 111 C to the power source (that is, the mouthpiece side opening 111 O) with respect to the reservoir 11. The supply port opens toward a predetermined direction (a downstream side in the predetermined direction A in FIG. 2), in which the aerosol atomized by the heating element 13 is directed toward the mouthpiece side opening 111 O, and the cap 16 is arranged to cover the supply port from the mouthpiece side opening 111 O. In the predetermined direction (the downstream side in the predetermined direction A in FIG. 2), in which the aerosol atomized by the heating element 13 is directed toward the mouthpiece side opening 111 O, the connection part 111 C, the reservoir 11, the cap 16 and the mouthpiece side opening 111 O are arranged in this order. The connection part 111 C, the reservoir 11, the cap 16 and the mouthpiece side opening 111 O are arranged on a straight line. The cap 16 is preferably fixed to the inhaler housing 110 X or/and the cylindrical member $\mathbf{14}_1$. At least one of the heating element 13 and the power supply member is damaged by a movement (here, movement to downstream) of separating the cap 16 from the reservoir 11.

Here, the power supply member may be any member as long as it electrically connects the heating element 13 and the power source. The power supply member is, for example, a lead wire (not shown in FIG. 2) for connecting the cylindrical member 14, the flange 17, or a lead wire connecting the cylindrical member 14 or the flange 17 to the power source. Although wiring of the lead wire is not particularly restricted, for example, the lead wire may be connected to the power source through the interior of the atomizing unit housing 111 X.

The flange 17 is formed of a conductive member and connected to the aforementioned lead wire for example. For instance, the flange 17 has a flange $\mathbf{17}_1$ connected to a lead wire extending from a first pole of the power source and a flange $\mathbf{17}_2$ connected to a lead wire extending from a second pole of the power source. The flange $\mathbf{17}_1$ is fixed to the cylindrical member $\mathbf{14}_1$, and the flange $\mathbf{17}_2$ is fixed to the cylindrical member $\mathbf{14}_2$. The flange $\mathbf{17}_1$ may be fixed to the cap 16. As described above, the flange 17 and the lead wire connected to the flange 17 are an example of a power supply member. The power supply member includes a first power supply portion (for example, the flange $\mathbf{17}_2$ and the lead wire connected to the flange $\mathbf{17}_2$) including a portion extending from the heating element 13 to the connection part 111 C to the power source, and a second power supply portion (for example, the flange $\mathbf{17}_1$ and the lead wire connected to the flange $\mathbf{17}_1$) including a portion extending from the heating element 13 to the opposite side of the connection part 111 C (that is, the mouthpiece side opening 111 O). In such a case, for example, the second power supply portion (for example, the lead wire connected to the flange $\mathbf{17}_1$ and the flange $\mathbf{17}_1$) is damaged by the movement (in this case, downstream movement) of separating the cap 16 from the reservoir 11.

Here, "damage" means an event degrading the function of each member. In the embodiment, it is to be noted that "damage" is a concept including a deformation of the heating element 13, poor contact between the cylindrical member 14 and the heating element 13, falling off of the flange $\mathbf{17}_1$, peeling of the lead wire from the flange $\mathbf{17}_1$, disconnection of the lead wire, etc.

In the embodiment, assuming the direction of separating the cap 16 from the reservoir 11 to be a separating direction, the power supply member is provided on the side of separating at least a part of the cap 16. The power supply member may be arranged to pass through the interior of the cap 16. The power supply member may be fixed to the cap 16.

For example, since the cap 16 is fixed to the cylindrical member $\mathbf{14}_1$, deformation of the heating element 13, poor contact between the cylindrical member 14 and the heating element 13 and the like occur along with the separation of the cap 16. Or, since the flange $\mathbf{17}_1$ is provided on the downstream end face of the cap 16, dropping of the flange 17, peeling of the lead wire from the flange 17, disconnection of the lead wire and the like occur along with the separation of the cap 16. Or, when the flange 17i is fixed to the cylindrical member 14₁ and the cap 16, deformation of the heating element 13, poor contact between the cylindrical member 14 and the heating element 13 and the like occur along with the separation of the cap 16.

In the embodiment, the heating element 13 is more easily damaged than the power supply member such as the cylindrical member 14, the flange 17 and the lead wire. The lead wire is more easily damaged than the cylindrical member 14 and the flange 17.

The aerosol source is a liquid such as glycerin or propylene glycol. The aerosol source is held, for example, by a porous body formed of a material such as a resin web as described above. The porous body may be formed of non-tobacco material or may be formed of tobacco material. The aerosol source may contain or may not contain an inhaling flavor component (nicotine component, etc.).

The electrical unit 112 includes an electrical unit housing 112 X constituting a part of the inhaler housing 110 X. In the embodiment, the electrical unit 112 has an inlet 112 A. As shown in FIG. 2, air flowing in from the inlet 112 A is guided to the atomizing unit 111 (the heating element 13). The electrical unit 112 includes a power source for driving the flavor inhaler 100 and a control circuit for controlling the flavor inhaler 100. The power source and the control circuit are accommodated in the electrical unit housing 112 X. The electrical unit housing 112 X has a cylindrical shape (for example, a tubular shape) extending along the predetermined direction A. The power source is, for example, a lithium ion battery. The control circuit is composed of, for example, a CPU and a memory.

The cartridge 130 is configured to be connectable to the inhaler body 110 constituting the flavor inhaler 100. The cartridge 130 is provided on the downstream side of the atomizing unit 111 in the air flow path communicating with the outlet 130 O (mouthpiece end) from the inlet 112 A. In other words, the cartridge 130 is not necessarily provided on the mouthpiece end side than the atomizing unit 111 in terms of physical space, and may be provided on the downstream side of the atomizing unit 111 on the air flow path leading aerosol generated by the atomizing unit 111 to the mouthpiece end side.

For example, the cartridge 130 includes a cartridge housing 131, a flavor source 132, a mesh 133 A, and a filter 133 B.

The cartridge housing 131 has a cylindrical shape (for example, a tubular shape) extending along the predetermined direction A. The cartridge housing 131 accommodates a flavor source 132. Here, the cartridge housing 131 is configured to be inserted into the inhaler housing 110 X along the predetermined direction A.

The flavor source 132 is provided downstream of the atomizing unit 111 on the air flow path. The flavor source 132 adds an inhaling flavor component to the aerosol generated by the aerosol source. In other words, flavor given to aerosol by the flavor source 132 is carried to the mouthpiece end.

In the embodiment, the flavor source 132 is formed of a raw material piece adding an inhaling flavor component to the aerosol generated by the atomizing unit 111. The size of the raw material piece is preferably 0.2 mm or more and 1.2 mm or less. Further, the size of the raw material piece is preferably 0.2 mm or more and 0.7 mm or less. Since a specific surface area increases as the size of the raw material piece forming the flavor source 132 is smaller, the inhaling flavor component is likely to be released from the raw material piece forming the flavor source 132. Therefore, when adding a desired amount of inhaling flavor component to the aerosol, the amount of the raw material piece can be decreased. As a raw material piece forming the flavor source 132, a shredded tobacco, a shaped product formed into a granular form of tobacco material can be used. However, the flavor source 132 may be a shaped product obtained by shaping tobacco material into a sheet. Further, the raw material piece forming the flavor source 132 may be made of plants (for example, mint, herb, etc.) other than tobacco. Perfume such as menthol may be added to the flavor source 132.

Here, the raw material piece forming the flavor source 132 is, for example, obtained by sieving according to JIS Z 8815 using a stainless sieve conforming to JIS Z 8801, for example. For example, using a stainless steel sieve having mesh size of 0.71 mm, a raw material piece passing through the stainless sieve having mesh size of 0.71 mm is obtained by sieving the raw material piece over 20 minutes by a dry and mechanical shaking method. Then, using the stainless steel sieve with a mesh size of 0.212 mm, a raw material piece passing through the stainless steel sieve with a mesh size of 0.212 mm is removed by sieving a raw material piece over 20 minutes by a dry and mechanical shaking method. That is, the raw material piece forming the flavor source 132 is a raw material piece, which passes through the stainless steel sieve (mesh size=0.71 mm) defining an upper limit and does not pass through a stainless steel sieve (mesh size=0.212 mm) defining a lower limit. Therefore, in the embodiment, the lower limit of the size of the raw material piece forming the flavor source 132 is defined by the mesh size of the stainless sieve defining the lower limit. The upper limit of the size of the raw material piece forming the flavor source 132 is defined by the mesh size of the stainless steel sieve defining the upper limit.

In the embodiment, the flavor source 132 is a tobacco source having an alkaline pH. The pH of the tobacco source is preferably greater than 7, more preferably 8 or more. This makes it possible to efficiently extract an inhaling flavor component generated by the tobacco source by aerosol. This makes it possible to decrease the amount of the tobacco source when adding a desired amount of the inhaling flavor component to the aerosol. On the other hand, the pH of the tobacco source is preferably 14 or less, more preferably 10 or less. As a result, it is possible to decrease damage (such as corrosion) to the flavor inhaler 100 (for example, the cartridge 130 or the inhaler body 110).

It should be noted that the inhaling flavor component generated by the flavor source 132 is being carried by the aerosol and heating of the flavor source 132 itself is unnecessary.

The mesh 133 A is provided to block the opening of the cartridge housing 131 upstream of the flavor source 132, and the filter 133 B is provided to block the opening of the cartridge housing 131 downstream of the flavor source 132. The mesh 133 A has roughness of a degree not to pass a raw material piece forming the flavor source 132. The roughness of the mesh 133 A has a mesh size of; for example, 0.077 mm or more and 0.198 mm or less. The filter 133 B is made of a substance with air permeability. The filter 133 B is preferably an acetate filter for example. The filter 133 B has roughness of a degree not to pass a material piece forming the flavor source 132.

(Use Mode of Non-Burning Type Flavor Inhaler)

Hereinafter, a use mode of the non-burning type flavor inhaler according to the embodiment will be described. Upon detecting the user's inhaling operation, the flavor inhaler 100 starts supplying the power supply output to the heating element 13. As the power supply output to the heating element 13 is started, atomization of the aerosol source held by the liquid holding member 12 is started. On the other hand, when the user's inhaling operation is not detected, the flavor inhaler 100 stops supplying the power supply output to the heating element 13. As the power supply output to the heating element 13 is stopped, the atomization of the aerosol source held by the liquid holding member 12 is stopped.

(Manufacturing Method of Atomizing Unit)

Figure 5A:
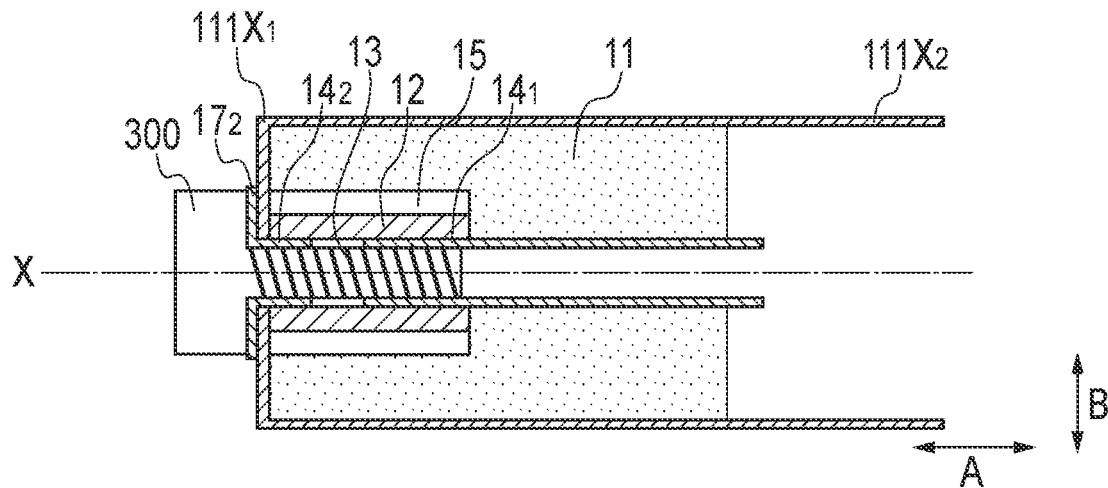
FIGS. 5 (A) to 5 (C) are diagrams for explaining a manufacturing method of an atomizing unit 111 according to an embodiment.
Figure 5B:
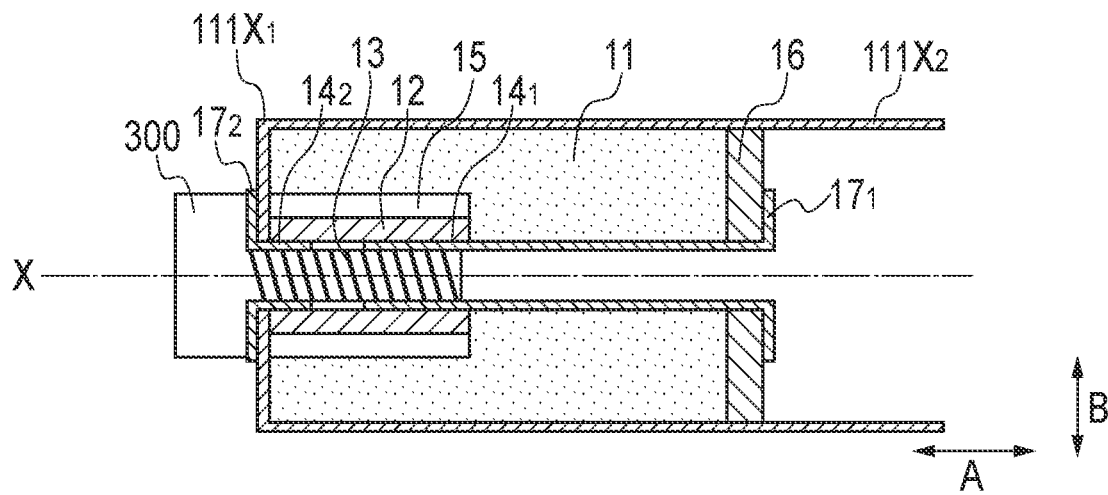

Hereinafter, a method of manufacturing the atomizing unit according to the embodiment will be described. FIGS. 4 and 5 are diagrams for explaining the manufacturing method of the atomizing unit 111 according to the embodiment.

As shown in FIG. 4 (A), the heating element 13 is arranged to follow a helical groove or projection formed on the side surface of the base member 300 having the axis X extending along the predetermined direction A (step A). In the embodiment, the base member 300 is a jig including a portion having a cylindrical shape.

Next, as shown in FIG. 4 (B), by sliding the cylindrical member $14_2$ with the flange $17_2$ fixed along the predetermined direction A, the cylindrical member $14_2$ is disposed on the outer side surface of the heating element 13, and by sliding the cylindrical member $14_1$ along the predetermined direction A, the cylindrical member $14_1$ is disposed on the outer side surface of the heating element 13 (step E). In such a case, in order to expose the heating portion 13 A of the heating element 13, the cylindrical member $14_1$ and the cylindrical member $14_2$ are disposed in being separated from each other.

Next, as shown in FIG. 4 (C), by sliding a housing cap body 111 $X_1$ constituting a part of the atomizing unit housing 111 X along the predetermined direction A, the housing cap body 111 $X_1$ is brought into contact with the flange $17_2$. Then, by sliding the liquid holding member 12 along the predetermined direction A, the liquid holding member 12 is disposed to contact or come close to at least a part (heating portion 13 A) of the heating element 13 (step C). The housing cap body 111 $X_1$ is fixed to the cylindrical member $14_2$ and the flange $17_2$.

The step of disposing the liquid holding member 12 to contact or come close to the heating portion 13 A of the heating element 13 may be a step of disposing the liquid holding member 12 to contact or come close to the heating portion A of the heating element 13 by the arrangement of the cover member 15 shown in FIG. 4 (D) to be described later. Further, the step of disposing the liquid holding member 12 may be a step of disposing the liquid holding member 12 while the liquid holding member 12 presses the outer side surface of the heating portion 13 A. The step of disposing the liquid holding member 12 may be a step of disposing the liquid holding member 12 to contact the entire circumference of the outer side surface of the heating portion 13 A. The step of disposing the liquid holding member 12 is a step of disposing the liquid holding member 12 on the outside of the heating element 13 when the heating element 13 is disposed on the outer side surface of the base member 300 (jig).

Next, as shown in FIG. 4 (D), by sliding the cover member 15 along the predetermined direction A, the cover member 15 is disposed on the outer side surface of the liquid holding member 12. By the displacement of the cover member 15, the heating portion 13 A of the heating element 13 comes into good contact with or comes close to the liquid holding member 12.

Next, as shown in FIG. 5 (A), the housing cylinder 111 $X_2$ constituting a part of the atomizing unit housing 111 X is fixed to the housing cap body 111 $X_1$. Then, the reservoir 11 is paced in the space formed by the housing cap body 111 $X_1$, the housing cylinder 111 $X_2$, and the cylindrical member 14. A part of the reservoir 11 is preferably placed also outside the cover member 15. The placement of the reservoir 11 may be performed before fixing the housing cylinder 111 $X_2$ to the housing cap body 111 $X_1$.

Here, it is preferable to fix the heating element 13 to the cylindrical member 14 after pacing the cylindrical member 14 on the outer side surface of the heating element 13. The step of fixing the heating element 13 and the cylindrical member 14 may be performed after the step shown in FIG. 4 (B) and before the step shown in FIG. 5 (B). The step of fixing the heating element 13 and the cylindrical member 14 are preferably performed before the step shown in FIG. 5 (A), more preferably before the step of FIG. 4 (C). This makes it possible to fix the heating element 13 and the cylindrical member 14 in a state in which there is no unnecessary member on the outer side surface of the cylindrical member 14. This makes it easy to fix the heating element 13 and the cylindrical member 14.

Next, as shown in FIG. 5 (B), after filling the reservoir 11 with the aerosol source, the downstream end of the reservoir 11 is covered by the cap 16. The cap 16 is fixed to the housing cylindrical 111 $X_2$. It is to be noted that the upstream end of the reservoir 11 is covered by the housing cap 111 $X_1$. Then, the flange $17_1$ is disposed on the downstream end face of the cap 16. The flange $17_1$ is fixed to the cylindrical member $14_1$.

Figure 5C:
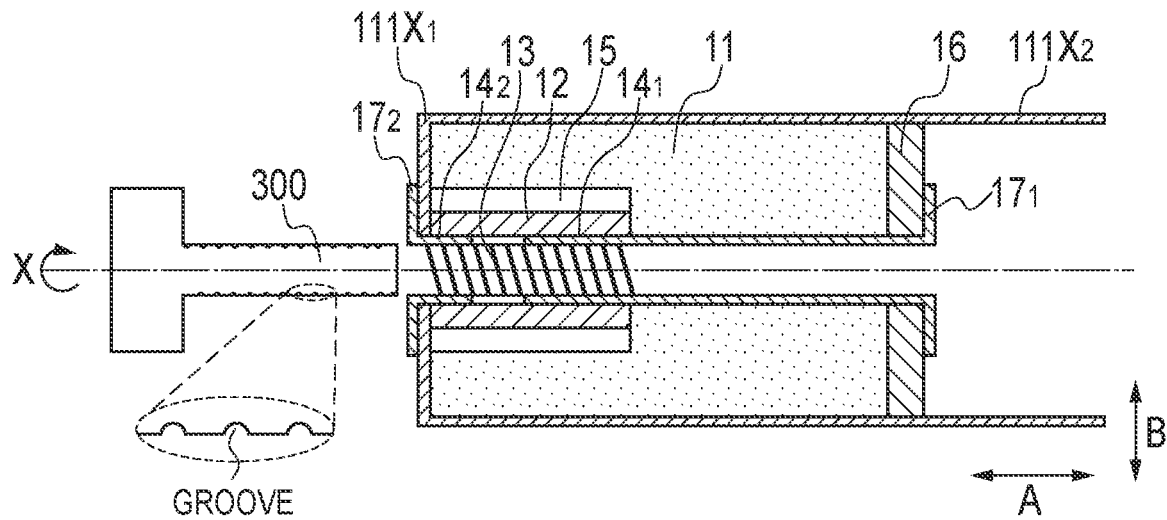
Figure 6A:
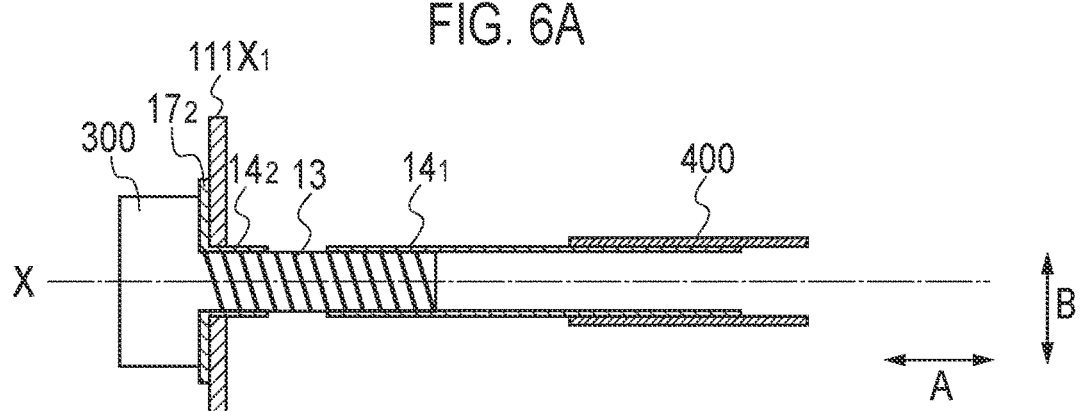
FIGS. 6 (A) to 6 (D) are diagrams for explaining a manufacturing method of an atomizing unit 111 according to a modification 1.
Figure 6B:
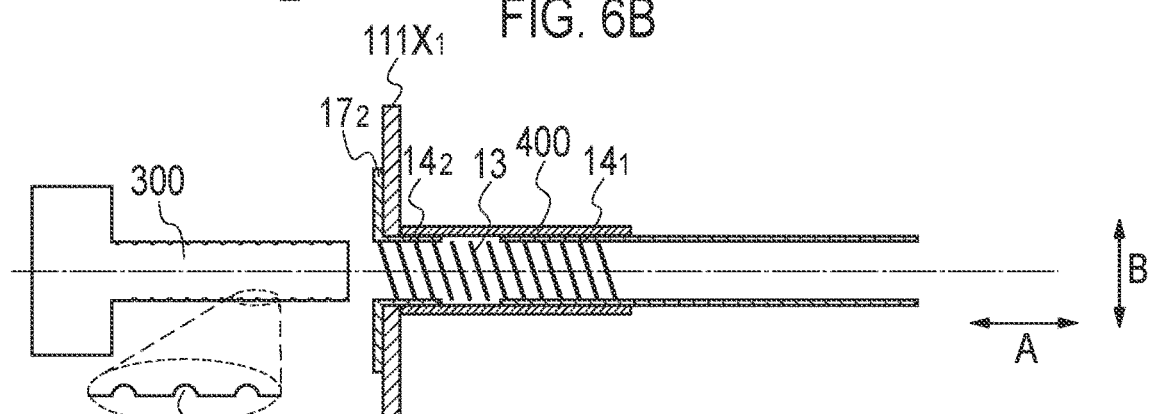
Figure 6C:
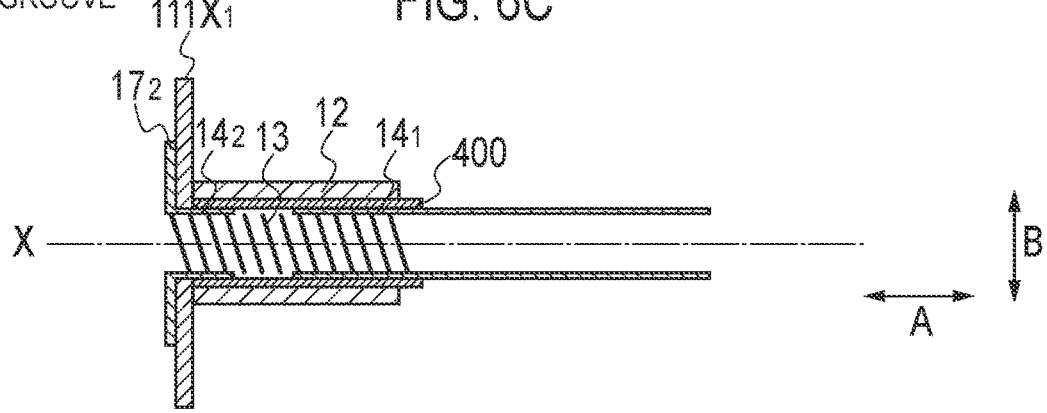
Figure 6D:
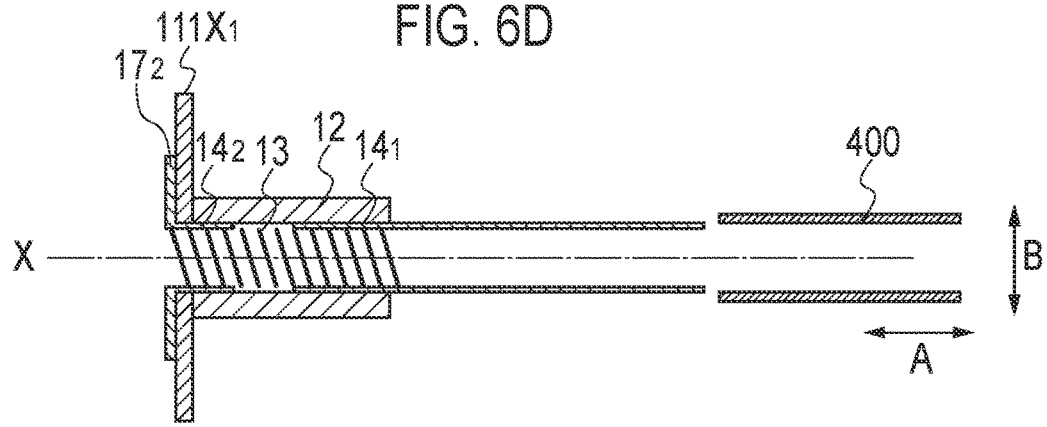

Next, as shown in FIG. 5 (C), the base member 300 (jig) is rotated about the axis X as a rotation axis to separate the whole heating element 13 from the groove or projection of the base member 300 (step B). Here, it should be noted that the cylindrical member 14 is fixed to the atomizing unit housing 111 X (the housing cap 111 $X_1$ and the housing cylinder 111 $X_2$) through the cap 16, the flange 17, and the like. Therefore, the step shown in FIG. 5 (C) is performed after fixing the cylindrical member 14 to the atomizing unit housing 111 X or/and after fixing the heating element 13 to the cylindrical member 14. Here, in the step shown in FIG. 5 (C), a space used as an air flow path is formed inside the heating element 13. The step shown in FIG. 5(C) is a step of forming, by separating the heating element 13, an aerosol intake (space between the cylindrical member $14_1$ and the cylindrical member $14_2$) that passes the aerosol atomized by the heating element 13. Since the aerosol intake communicates with the inside of the heating element 13 only by separating the heating element 13 from the base member 300, it should be noted that the step shown in FIG. 5 (C) is a step of forming the aerosol intake.

Further, the step shown in FIG. 5 (C) is a step of forming at least a part of the air flow path inside the heating element 13 by the separation of the heating elements 13. Specifically, in the step shown in FIG. 5 (C), the whole heating element 13 is separated from the base member 300 (jig), and at least a part of the air flow path is formed inside the heating element 13 by the separation of the heating elements 13. In such a case, before the step shown in FIG. 5 (C), it is preferable to perform a step (step G) of disposing a flow path forming member forming at least a part of the air flow path. The flow path forming member, for example, may be considered as the above-described cylindrical member 14.

Therefore, the step of disposing the flow path forming member may be considered as the step shown in FIG. 4 (B).

In the embodiment, the depth of the groove of the base member 300 or the height of the projection of the base member 300 is preferably the same or less than the diameter of the wire forming the heating element 13 from the viewpoint of electrical connection between the cylindrical member 14 and the heating element 13. On the other hand, the depth of the groove of the base member 300 or the height of the projection of the base member 300 is preferably half or more of the diameter of the wire forming the heating element 13 from the viewpoint of holding the heating element 13 by the base member 300.

Operation and Effect

In the embodiment, at least a part of the outer side surface of the liquid holding member 12 in the orthogonal direction B is covered with the cover member 15. With such a configuration, it is possible to prevent a situation (oversupply) in which the aerosol source is excessively supplied to the liquid holding member 12. The prevention of the oversupply lowers a risk of leakage. In addition, the prevention of the oversupply decreases a heat loss in thermal atomization, and restricts a reduction of atomization efficiency.

Here, the cover member 15 is formed of a liquid impermeable member. As a result, oversupply of the aerosol source is suppressed. The cover member 15 is preferably formed of a member having a thermal conductivity lower than the thermal conductivity of the aerosol source or the liquid holding member 12. With such a configuration, a heat loss in thermal atomization is suppressed. The cover member 15 is preferably formed of a member that presses the liquid holding member 12 in the inward direction. With such a configuration, the liquid holding member 12 can be brought into good contact with or close to the heating element 13.

In the embodiment, it is preferable that the cover member 15 covers the outer side surface of the liquid holding member 12 over the entire length of the outer side surface of the liquid holding member 12 along the predetermined direction A in the range where the inner side surface of the liquid holding member 12 and the heating element 13 (the heating portion 13 A) contact or come close to each other. With such a configuration, the above-described oversupply can be further decreased.

In the embodiment, it is preferable that the cover member 15 covers the outer side surface of the liquid holding member 12 over the entire circumference of the outer side surface of the liquid holding member 12 in the circumferential direction around the predetermined direction A as an axis in the range where the inner side surface of the liquid holding member 12 and the heating element 13 (the heating portion 13 A) contact or come close to each other. With such a configuration, the above-described oversupply can be further decreased.

In the embodiment, it is preferable that the cover member 15 uniformly covers the outer side surface of the liquid holding member 12. With such a configuration, it is possible to uniformly supply the aerosol source to the heating element 13 (heating portion 13 A) and to improve the atomization efficiency. For example, the cover member 15 may have no opening and cover the outer side surface of the liquid holding member 12. This makes it possible to more effectively suppress the above-described oversupply. Or, the cover member 15 may have ten or more equally spaced openings. By adjusting the number and size of the 10 or more equally spaced openings, it is possible not only to decrease the above-described oversupply, but also to adjust the supply amount of the aerosol source to a desired amount, and to easily supply an equal amount of the aerosol source, improving the atomization efficiency. Or, the cover member 15 has a plurality of equally spaced openings, and the covering area, which is the area of the outer side surface of the liquid holding member 12 covered by the cover member 15, may be 60% or more of the area of the outer side surface of the liquid holding member 12. With such a configuration, the aerosol source supply amount can be more effectively decreased.

In the embodiment, it is preferable that the thickness of the liquid holding member 12 covered with the cover member 15 is smaller than the thickness of the liquid holding member 12 not covered with the cover member 15, in other words, a configuration that the liquid holding member 12 is compressed by the cover member 15 is preferable. With such a configuration, a situation that an excessive amount of the aerosol source is held by the liquid holding member 12 is decreased by the compression of the liquid holding member 12.

In the embodiment, at least a part of the reservoir 11 is preferably arranged outside the cover member 15 in the orthogonal direction B. With such a configuration, it is possible to decrease the oversupply described above by the cover member 15, while increasing the capacity of the reservoir 11 (that is, the amount of aerosol source storable by the reservoir 11) by allocating the space outside the cover member 15 to the reservoir 11.

In the embodiment, the cylindrical member 14 constitutes a barrier member having an outer side surface located between the outer side surface of the heating element 13 and the inner side surface of the cover member 15 in the orthogonal direction B. It is preferable that the outer side surface of the cylindrical member 14 is provided at a position facing a part of the inner side surface of the liquid holding member 12. Further, it is preferable that the outer side surface of the cylindrical member 14 is provided at a position facing a part of the inner side surface of the cover member 15. With such a configuration, deformation of the heating element 13 due to a stress in the inward direction of the liquid holding member 12 covered by the cover member 15 is suppressed. Further, when the cylindrical member 14 constitutes an air flow path and has a predetermined strength (for example, strength to withstand a stress of the cover member 15 pressing the outer side surface of the cylindrical member 14 in the inward direction in the orthogonal direction B), deformation of the heating element 13 due to the stress of the cover member 15 and deformation of the air flow path are suppressed. In other words, in an aspect where the inside of the cylindrical member 14 is an air flow path, the cylindrical member 14 functions as a barrier member in terms of suppressing deformation of the heating element 13 and deformation of the air flow path due to the stress of the cover member 15.

In the embodiment, the cylindrical member 14 forming at least a part of the air flow path is formed of a conductive member, and includes a cylindrical member $14_1$ contacting the first end portion $13\ B_1$ at the first contact point and a cylindrical member $14_2$ contacting the second end portion $13\ B_2$ at the second contact point. Therefore, it is possible to reduce the number of components required for forming the air flow path and forming the electrical contact.

In the embodiment, a cap 16 is provided to cover the supply port for supplying the aerosol source to the reservoir 11. At least one of the heating element 13 and the power supply member is damaged by a movement (here, downstream movement) of separating the cap 16 from the reservoir 11. Therefore, the use of the flavor inhaler 100 accompanied by reinjection of the aerosol source to the reservoir 11 can be effectively decreased. Since the cap 16 covers the supply port provided on the opposite side of the connection part 111 C to the power source with reference to the reservoir, the use of the flavor inhaler 100 accompanied by the reinjection of the aerosol source is effectively decreased.

In the embodiment, the power supply member includes a first power supply portion (e.g, the flange $17_2$ and a lead wire connected to the flange $17_2$) including a portion extending from the heating element 13 to the power source connection part 111 C side, and a second power supply portion (e.g, the flange $17_1$ and a lead wire connected to the flange $17_1$) including a portion extending from the heating element 13 to the opposite side of the connection part 111 C (that is, the mouthpiece side opening 111 o). Therefore, it is easy to adopt a configuration in which the second power supply portion is damaged by the movement (here, downstream movement) of separating the cap 16 from the reservoir 11.

In the embodiment, a coil forming the heating element 13 includes a heating portion 13 A formed of a wire between the first contact and the second contact arranged closest to each other on the wire, a first end portion 13 $B_1$ formed on the wire by a wire on one outer side of the heating portion 13 A on the wire, and a second end portion 13 $B_2$ formed on the wire by a wire on the other outer side of the heating portion 13 A. At least a part of the inner side surface of the liquid holding member 12 contacts or comes close to the heating portion 13 A. In other words, since the end portion (the first end portion 13 $B_1$ and the second end portion 13 $B_2$ in the embodiment) having a high possibility of poor quality is not used as a heating portion, and the end portion other than the end portion of the wire forming the heating element 13 (coil) (the heating portion 13 A in the embodiment) is used as a heating portion, it is possible to improve the uniformity of the aerosol generation amount without depending on the manufacturing method of the heating element 13.

In the embodiment, since only the central portion of the heating element 13 (coil) is used as the heating portion 13 A, the liquid holding member 12 can be easily disposed over the entire central portion used as the heating member 13 A, and the atomizing unit 111 with little energy loss can be easily formed.

In the embodiment, the cylindrical member 14 is formed of a conductive member, and includes a cylindrical member $14_1$ contacting the first end portion 13 $B_1$ at the first contact point and a cylindrical member $14_2$ contacting the second end portion 13 $B_2$ at the second contact point. The cylindrical member $14_1$ and the cylindrical member $14_2$ are disposed on the side surface (in the embodiment, the outer side surface) of the heating element 13. The side surface of the heating element 13 means the outer peripheral surface and the inner peripheral surface of the coil when considering the coil forming the heating element 13 as a cylindrical member. Therefore, the side surface of the heating element 13 is actually constituted by the side surface of the wire forming the coil. With the configuration described above, by making contact with the cylindrical member 14 on the side surface of the heating element 13, it is possible to make electrical connection on the surface and realize stable electrical connection. In addition, in the case of making electrical connection with fixation to the cylindrical member 14 on the side surface of the heating element 13, fixation on the surface is possible, and the heating element 13 can be firmly fixed to the cylindrical member 14. In addition, fixing such as welding is easy to perform.

Furthermore, in the embodiment, since the cylindrical member 14 is a member having a surface, it is possible to make electrical connection between surfaces and realize stable electrical connection, and the heating element 13 can be firmly fixed to the cylindrical member 14. Further, fixing by welding becomes easy.

In the embodiment, the cylindrical member $14_1$ is disposed between the liquid holding member 12 and the first end portion 13 $B_1$ in the orthogonal direction B, and the cylindrical member $14_2$ is disposed between the liquid holding member 12 and the second end portion 13 $B_2$. Therefore, since the heating element 13 is supported by the cylindrical member $14i$ and the cylindrical member $14_2$, deformation of the heating element 13 is prevented even if the inside of the heating element 13 is hollow.

In the embodiment, the manufacturing method of the atomizing unit 111 includes steps of disposing the heating element 13 to follow a helical groove or a projection formed on the side surface of the base member 300 (jig) having the axis X extending along the predetermined direction A, and rotating the base member 300 about the axis X to separate the whole heating elements 13 from the groove or projection of the base member 300. In other words, since the heating member 13 is supported by the base member 300 in the manufacturing process of the atomizing unit 111, it is possible to prevent deformation of the heating element 13 in the manufacturing process of the atomizing unit 111, and manufacture the atomizing unit 111 having the heating element 13 with high quality.

In the embodiment, after bringing the liquid holding member 12 into contact with or close to the heating portion 13 A of the heating element 13, the base member 300 (jig) is rotated about the axis X as a rotation axis to separate the whole heat generating body 13 from the groove or projection of the base member 300. Therefore, it is possible to prevent the deformation of the heating element 13 by the step of disposing the liquid holding member 12 to contact or come close to the heating part 13 A of the heat generating element 13 (in particular, the step of bringing the heating part 13 A into contact with or close to the liquid holding member 12). This makes it possible to manufacture the atomizing unit 111 with the high-quality heating element 13.

In the embodiment, the base member 300 (jig) is rotated about the axis X as a rotation axis, and before the whole heating element 13 is separated from the groove or the projection of the base member 300, the cylindrical member 14 is disposed on the outer side surface of the heating element 13 in the orthogonal direction. In other words, the heating member 13 is always supported by the base member 300 or the cylindrical member 14 in the manufacturing process of the atomizing unit 111. Therefore, it is possible to always suppress the deformation of the heating element 13 in the manufacturing process of the atomizing unit 111, and to manufacture the atomizing unit 111 having the high-quality heating elements 13.

The step of disposing the liquid holding member 12 may be a step of disposing the liquid holding member 12 while the liquid holding member 12 presses the outer side surface of the heating portion 13 A. The step of disposing the liquid holding member 12 may be a step of disposing the liquid holding member 12 to contact the entire circumference of the outer side surface of the heating portion 13 A. In these cases, since the liquid holding member 12 is disposed before separating the heating element 13 from the base member 300, it is possible to prevent the deformation of the heating element 13 in the step of disposing the liquid holding member 12, and to manufacture the atomizing unit 111 with the high-quality heating element 13.

In addition, by the separation of the heating elements 13, at least a part of the air flow path may be formed inside the heating element 13. As a result, before the heating element 13 is separated from the base member 300, ingress of foreign matter into the air flow path is prevented.

In the embodiment, after fixing the cylindrical member 14 to the atomizing unit housing 111 X or/and after fixing the heating element 13 to the cylindrical member 14, the base member 300 (jig) is rotated about the axis X as a rotation axis to separate the whole heating element 13 from the groove or projection of the base member 300. As a result, it is possible to prevent the deformation of the heating element 13 accompanied by the rotation of the base member 300, and to manufacture the atomizing unit 111 with the high-quality heating element 13.

Modification 1

Hereinafter, a modification 1 of the embodiment will be described. Differences from the embodiment will mainly be described below.

In the modification 1, a description will be given on an example of a step (step shown in FIG. 4 (C)) of disposing the liquid holding member 12 to contact or come close to the heating portion 13 A of the heating element 13. FIG. 6 is a diagram for explaining a modification example of the process shown in FIG. 4 (C). However, it should be noted that the modification 1 is different from the embodiment in that the step of rotating the base member 300 (jig) about the axis X as a rotation axis to separate the whole heating elements 13 from the groove or projection of the base member 300 is performed in the middle of the process shown in FIG. 4 (C).

Specifically, as shown in FIG. 6 (A), by sliding a sliding member 400 having a cylindrical shape along the predetermined direction A, the sliding member is disposed on the outer side surfaces of the heating element 13 and the cylindrical member 14. That is, the sliding member 400 is slid along the outer side surfaces of the heating element 13 and the cylindrical member 14 in the orthogonal direction B (step C 1).

Next, as shown in FIG. 6 (B), the base member 300 (jig) is rotated about the axis X as a rotation axis to separate the whole heating elements 13 from the groove or projection of the base member 300 (step B). Here, it should be noted that the cylindrical member 14 is fixed to the atomizing unit housing 111 X (the housing cap body 111 $X_1$) via the flange 17 and the like.

Next, as shown in FIG. 6 (C), the liquid holding member 12 is slid along the outer side surface of the sliding member 400 in the orthogonal direction B (step C 2). Here, since the heating element 13 is covered with the sliding member 400, even if the liquid holding member 12 is disposed in a state where the whole heating element 13 is separated from the base member 300 (jig), deformation of the heating element 13 accompanied by the disposition of the liquid holding member 12 is prevented.

Next, as shown in FIG. 6 (D), the sliding member 400 is removed by sliding the sliding member 400 in the predetermined direction A. That is, the sliding member 400 is removed by sliding from between the liquid holding member 12 and the heating element 13 (step C 3). It should be noted that the liquid holding member 12 is placed to contact or come close to the heating portion 13 A of the heating element 13.

In such a case, it is preferable that the sliding member 400 is constituted by a member that is more likely to slide in the predetermined direction A than the liquid holding member 12. For example, the sliding member 400 is configured so that a frictional force (dynamic frictional force or/and static frictional force) acting between the inner side surface of the sliding member 400 and the outer side surface of the cylindrical member 14 is smaller than the frictional force between the inner side surface of the liquid holding member 12 and the outer side surface of the cylindrical member 14. With this configuration, it becomes easier to dispose the liquid holding member 12 by sliding by using the sliding member 400, as compared with the case where the liquid holding member 12 is disposed as a single unit. In such a case, the rigidity of the sliding member 400 is preferably higher than that of the liquid holding member 12. With this configuration, as compared with the case where the liquid holding member 12 is disposed as a single unit, the use of the sliding member 400 makes it easier to dispose the liquid holding member 12, because when sliding the sliding member 400 between the cylindrical member $14_1$ and the cylindrical member $14_2$, it becomes difficult to be caught by a cut of the cylinder.

In the example shown in FIG. 6, the sliding member 400 is slid along the outer side surface of the cylindrical member 14, and then the liquid holding member 12 is slid along the outer side surface of the sliding member 400. However, the modification 1 is not limited thereto. Specifically, after inserting the sliding member 400 inside the liquid holding member 12, in a state where the sliding member 400 is inserted inside the liquid holding member 12, the sliding member 400 may be slid along the outer side surface of the cylindrical member 14.

In the example shown in FIG. 6, the sliding member 400 is removed by sliding after separating the heating element 13 from the groove or projection of the base member 300. The modification 1 is not limited thereto. Specifically, the step of removing the sliding member 400 by sliding may be performed before the step of separating the heating element 13 from the groove or projection of the base member 300.

In the modification 1, the depth of the groove of the base member 300 or the height of the projection of the base member 300 is equal to or less than the diameter of the wire constituting the heating element 13, preferably equal to or more than half the diameter of the wire.

In the modification 1, the step of separating the heating element 13 from the groove or the projection of the base member 300 is, as in the embodiment, preferably performed after fixing the cylindrical member 14 to the atomizing unit housing 111 X or/and after fixing the heating element 13 to the cylindrical member 14.

Operation and Effect

In the modification 1, the heating element 13 is separated from the groove or the projection of the base member 300 before disposing the liquid holding member 12 to contact or come close to the heating portion 13 A of the heating element 13. In this manner, the base member 300 can be separated as fast as possible before assembling members such as the liquid holding member 12, so that the base member 300 can be diverted to the next semi-finished product in a short time, improving the productivity of the atomizing unit 111.

While obtaining such an effect, by using the sliding member 400, in the step of disposing the liquid holding member 12 to contact or come close to the heating portion 13 A of the heating element 13 (for example, the step of sliding the liquid holding member 12), it is possible to prevent the deformation of the heating element 13, and to manufacture the atomizing unit 111 with the high-quality heating element 13. Further, this makes it easy to dispose the liquid holding member 12 on the outer side surfaces of the heating element 13 and the cylindrical member 14.

Modification 2

Hereinafter, a modification 2 of the embodiment will be described. Differences from the embodiment will mainly be described below.

Figure 7A:
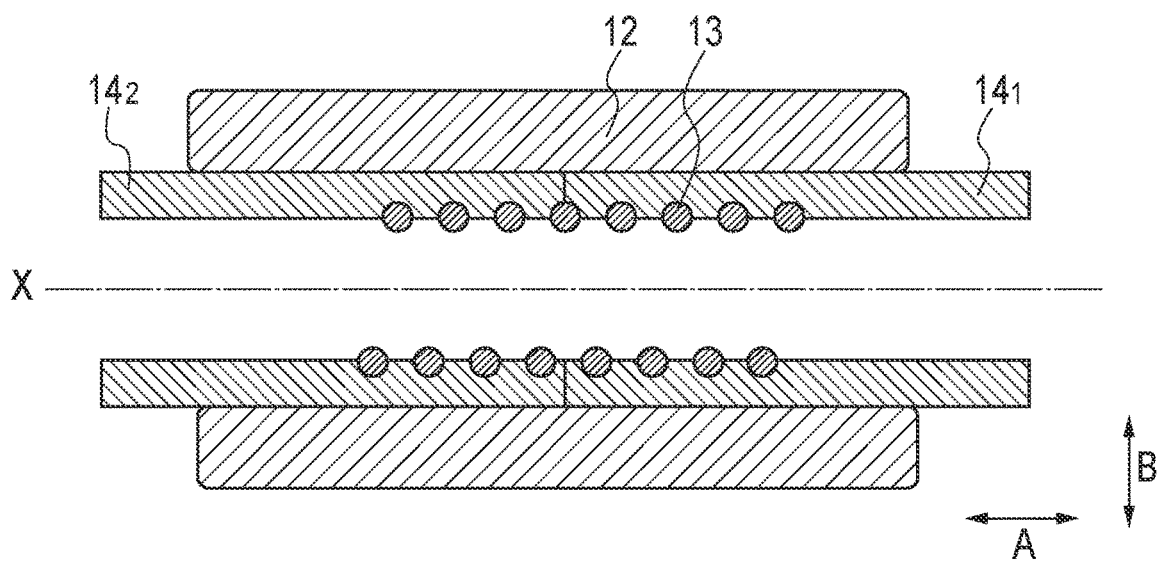
FIGS. 7 (A) and 7 (B) are diagrams for explaining a manufacturing method of an atomizing unit 111 according to a modification 2.
Figure 7B:
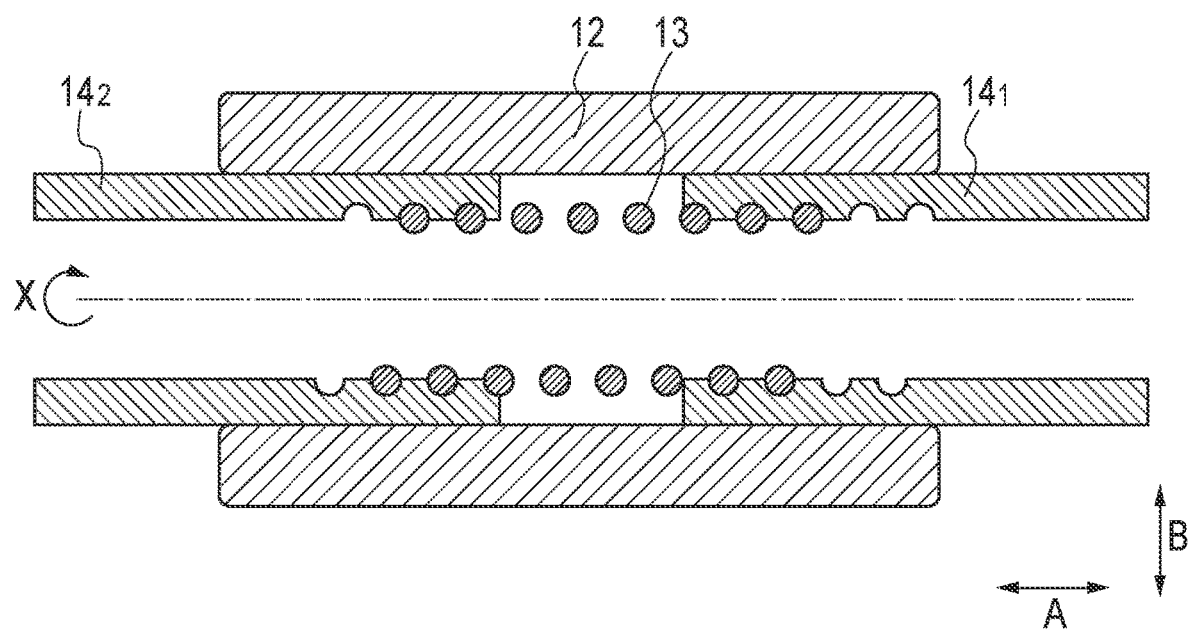

In the embodiment, the base member 300 is a jig having a cylindrical shape. In contrast, in the modification 2, a case where the base member 300 is the cylindrical member 14 (the cylindrical member $14_1$ and the cylindrical member $14_2$) is exemplified. FIG. 7 is a diagram for explaining a method of manufacturing the atomizing unit 111 according to the modification 2. In FIG. 7, it should be noted that the atomizing unit housing 111 X, the cap 16, the flange 17 and the like are omitted.

Specifically, as shown in FIG. 7 (A), the heating element 13 is disposed to follow a helical groove or a projection formed on the inner side surface of the cylindrical member 14 having an axis X extending along the predetermined direction A, and the cylindrical member 14 and the heating element 13 are electrically connected (step A and step D). Here, the cylindrical member 14 is disposed outside the heating element 13.

In the modification 2, the cylindrical member $14_1$ and the cylindrical member $14_2$ are continuous in the predetermined direction A. In other words, the step A is a step of disposing the heating element 13 across both the cylindrical member $14_1$ and the cylindrical member $14_2$.

Here, it should be noted that the liquid holding member 12 is disposed on the outer side surface of the cylindrical member 14 (the cylindrical member $14_1$ and the cylindrical member $14_2$) in the orthogonal direction B.

Next, in FIG. 7 (B), at least one of the cylindrical member $14_1$ and the cylindrical member $14_2$ is rotated about the axis X as a rotation axis to separate the heating element 13 from the groove or the projection (step B). That is, the step B is a step of separating the cylindrical member $14_1$ and the cylindrical member $14_2$ from each other, while maintaining the state in which the heating element 13 is disposed over both the cylindrical member $14_1$ and the cylindrical member $14_2$.

In the modification 2, by separating the cylindrical member $14_1$ and the cylindrical member $14_2$ from each other, the heating portion 13 A of the heating element 13 is exposed to the liquid holding member 12. The liquid holding member 12 is disposed to contact or come close to the heating portion 13 A of the heating element 13 (step C or step C 4). Since a space between the cylindrical member $14_1$ and the cylindrical member $14_2$ is formed for the first time in the step shown in FIG. 7 (B), the step shown in FIG. 7 (B) is a step of forming the aerosol intake (space between the cylindrical member $14_1$ and the cylindrical member $14_2$) to pass aerosol atomized by the heating element 13 to the inside of the heating element 13 by the separation of the heating element 13.

Here, in the case of fixing the heating element 13 to the cylindrical member 14, such a fixing step may be performed after the step shown in FIG. 7 (B). Alternatively, in the cylindrical member $14_1$ and the cylindrical member $14_2$, after fixing the conductive member and the heating element 13 in one of them, the conductive member in the other of them may be separated from the conductive member in the one of them. The step (step D) of electrically connecting the cylindrical member 14 and the heating element 13 may be considered as such a fixing step.

The cylindrical member $14_1$ and the cylindrical member $14_2$ may be connected by screwing in a state before separating the cylindrical member $14_1$ and the cylindrical member $14_2$ from each other (i.e., in the state shown in FIG. 7 (A)).

Operation and Effect

In the modification 2, the heating element 13 is disposed to follow the helical groove or projection formed on the inner side surface of the cylindrical member 14, and one of the cylindrical member $14_1$ and the cylindrical member $14_2$ is rotated to separate from the groove or the projection of the heating element 13. That is, in the manufacturing process of the atomizing unit 111, since the heating element 13 is supported by the cylindrical member $14_1$ and the cylindrical member $14_2$, it is possible to prevent deformation of the heating element 13, and to manufacture the atomizing unit 111 with the high-quality heating element 13.

In the modification 2, since the cylindrical member 14 is used as a base member 300, an extra jig used for forming the heating element 13 as in the embodiment is unnecessary, and the manufacturing process of the atomizing unit 111 can be simplified.

Modification 3

Hereinafter, a modification 3 of the embodiment will be described. Differences from the modification 2 will be mainly described below.

In the modification 2, the heating element 13 is disposed to follow the helical groove or projection formed on the inner side surface of the cylindrical member 14. On the other hand, in the modification 3, the heating element 13 is disposed to follow the helical groove or projection formed on the outer side surface of the cylindrical member 14.

Figure 8A:
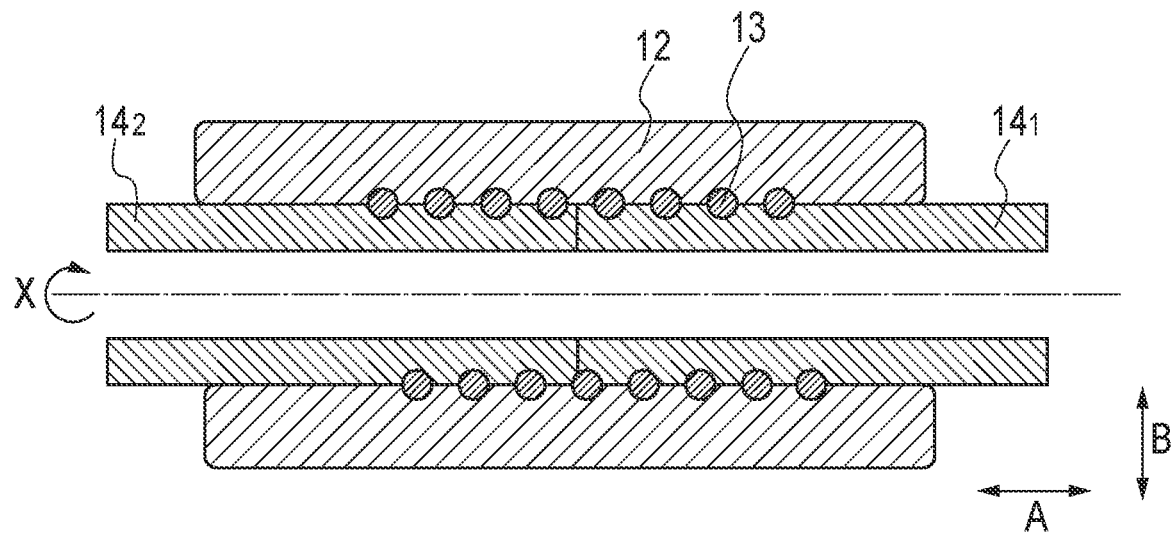
FIGS. 8 (A) and 8 (B) are diagrams for explaining a manufacturing method of an atomizing unit 111 according to a modification 3.
Figure 8B:
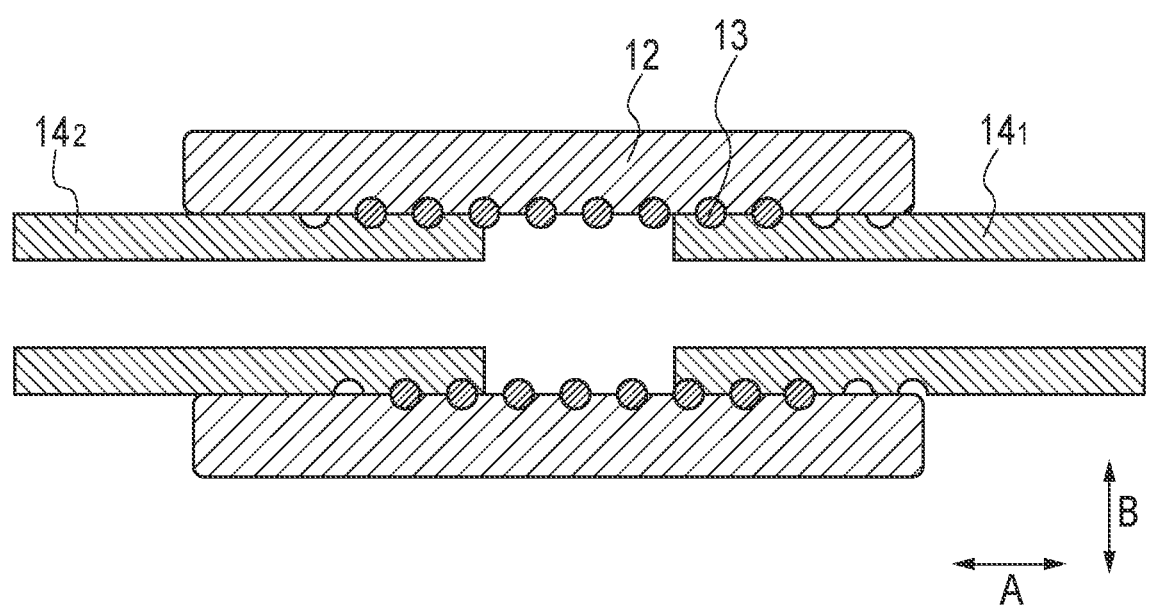

Specifically, as shown in FIG. 8 (A), a heating element 13 is disposed to follow a helical groove or projection formed on the outer side surface of the cylindrical member 14 having an axis X extending along a predetermined direction A, and the cylindrical member 14 and the heating element 13 are electrically connected (Step A and Step D). Here, the cylindrical member 14 is disposed inside the heating element 13.

Next, in FIG. 8 (B), at least one of the cylindrical member $14_1$ and the cylindrical member $14_2$ is rotated about the axis X as a rotation axis to separate the heating element 13 from the groove or the projection (step B). Since the space between the cylindrical member $14_1$ and the cylindrical member $14_2$ is formed for the first time in the step shown in FIG. 8 (B), the step shown in FIG. 8 (B) is a step of forming the aerosol intake (the space between the cylindrical member $14_1$ and the cylindrical member $14_2$) to pass the aerosol atomized by the heating element 13 to the inside of the heating element 13 by the separation of the heating element 13.

Operation and Effect

In the modification 3, as in the modification 2, it is possible to manufacture the atomizing unit 111 with the high-quality heating element 13, and to simplify the manufacturing process of the atomizing unit 111.

Modification 4

Hereinafter, a modification 4 of the embodiment will be described. Differences from the embodiment will mainly be described below.

Figure 9:
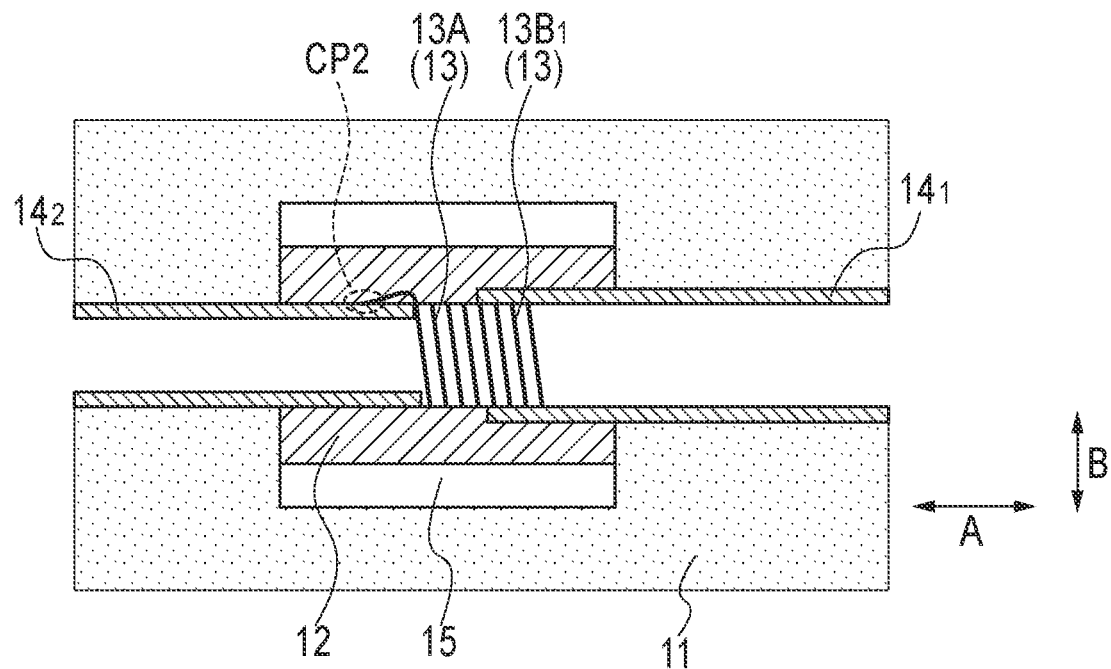
FIG. 9 is a diagram showing an atomizing unit 111 according to a modification 4.

In the embodiment, the inner diameter of the cylindrical member $14_1$ is the same as the inner diameter of the cylindrical member $14_2$. In contrast, in the modification 4, as shown in FIG. 9, the inner diameter and the outer diameter of the cylindrical member $14_1$ are larger than the inner diameter and the outer diameter of the cylindrical member $14_2$. In FIG. 9, it should be noted that the atomizing unit housing 111 X, the cap 16, the flange 17 and the like are omitted.

In such a case, as shown in FIG. 9, the heating element 13 has the heating portion 13 A and the first end portion $13\ B_1$, but does not have the second end portion $13\ B_2$. The outer side surface of the first end portion $13\ B_1$ contacts the inner side surface of the cylindrical member $14_1$. In other words, the cylindrical member $14_1$ is disposed outside the heating element 13. On the other hand, a lead wire drawn upstream from the heating portion 13 A is connected to the outer side surface or the end face of the cylindrical member $14_2$. Here, the lead wire is made of the same member (for example, a nichrome wire) as the heating element 13. The lead wire may be a member in which the wire forming the heating element 13 is extended as it is. The outer side surface or the end face of the cylindrical member $14_2$ and the lead wire form the second contact CP 2. The lead wire is fixed to the outer side surface of the cylindrical member $14_1$ by welding or soldering.

In FIG. 9, it should be noted that the lead wire is inflated for convenience of illustration, but the lead wire is actually disposed between the liquid holding member 12 and the cylindrical member 14.

Operation and Effect

In the modification 4, the outer diameter of the cylindrical member $14_1$ provided on the downstream side is larger than the outer diameter of the cylindrical member $14_2$ provided on the upstream side. Therefore, the distance between the cover member 15 and the cylindrical member $14_1$ is smaller than the distance between the cover member 15 and the cylindrical member $14_2$, and it is possible to prevent the oversupply of the aerosol source to the liquid holding member 12 on the downstream side.

In the modification 4, the cylindrical member $14_1$ is disposed between the liquid holding member 12 and the first end portion $13\ B_1$ in the orthogonal direction B. Therefore, since the heating element 13 is supported by the cylindrical member $14_1$, deformation of the heating element 13 is prevented even if the inside of the heating element 13 is hollow.

Modification 5

Hereinafter, a modification 5 of the embodiment will be described. Differences from the embodiment will mainly be described below.

Figure 10:
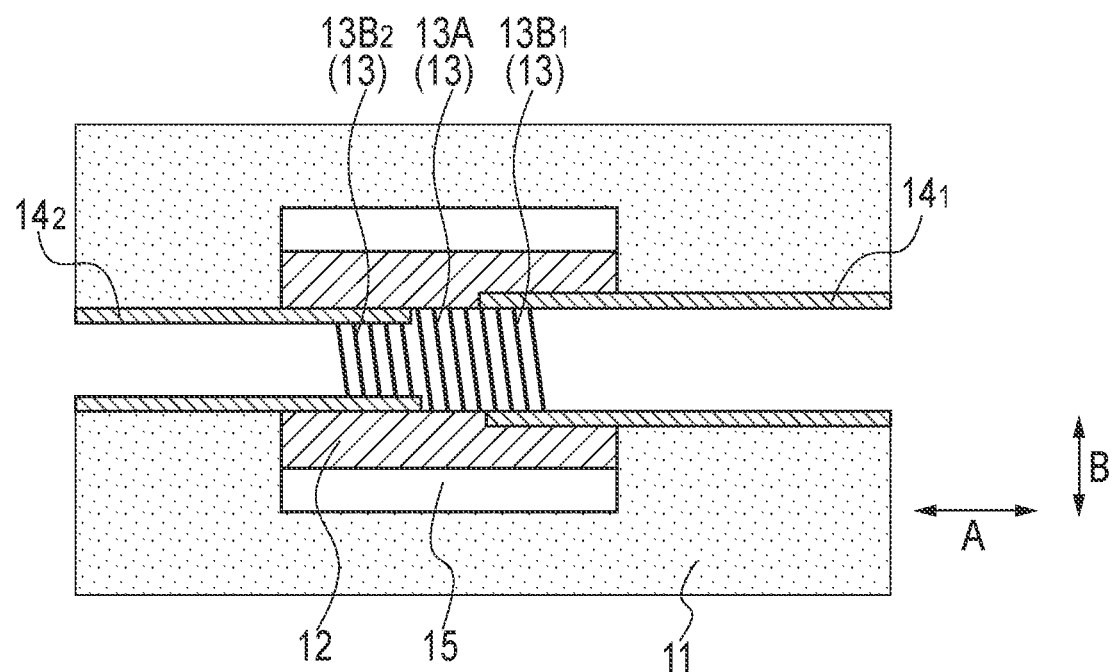
FIG. 10 is a diagram showing an atomizing unit 111 according to a modification 5.

In the embodiment, the inner diameter of the cylindrical member $14_1$ is the same as the inner diameter of the cylindrical member $14_2$. In contrast, in the modified example 4, as shown in FIG. 10, the inner diameter and the outer diameter of the cylindrical member $14_1$ are larger than the inner diameter and the outer diameter of the cylindrical member $14_2$. In FIG. 10, it should be noted that the atomizing unit housing 111 X, the cap 16, the flange 17 and the like are omitted.

In this case, as shown in FIG. 10, the heating element 13 has a heating portion 13 A, a first end portion $13\ B_1$ and a second end portion 13 B 2. However, the outer diameter of the second end portion $13\ B_2$ is smaller than the outer diameter of the first end portion $13\ B_1$. The outer side surface of the first end portion $13\ B_1$ contacts the inner side surface of the cylindrical member $14_1$. Similarly, the outer side surface of the second end portion $13\ B_2$ contacts the inner side surface of the cylindrical member $14_2$. In other words, the cylindrical member $14_1$ and the cylindrical member $14_2$ are disposed outside the heating element 13.

Operation and Effect

In the modification 5, the outer diameter of the cylindrical member $14_1$ provided on the downstream side is larger than the outer diameter of the cylindrical member $14_2$ provided on the upstream side. Therefore, as in the modification 4, the distance between the cover member 15 and the cylindrical member $14_1$ is smaller than the distance between the cover member 15 and the cylindrical member $14_2$, and it is possible to suppress the oversupply of the aerosol source to the liquid holding member 12 on the downstream side.

In the modification 5, the cylindrical member $14_1$ is disposed between the liquid holding member 12 and the first end portion $13\ B_1$ in the orthogonal direction B, and the cylindrical member $14_2$ is disposed between the liquid holding member 12 and the second end portion $13\ B_2$. Therefore, since the heating element 13 is supported by the cylindrical member $14_1$, deformation of the heating element 13 is suppressed even if the inside of the heating element 13 is hollow.

Modification 6

Hereinafter, a modification 6 of the embodiment will be described. Differences from the embodiment will mainly be described below.

Figure 11:
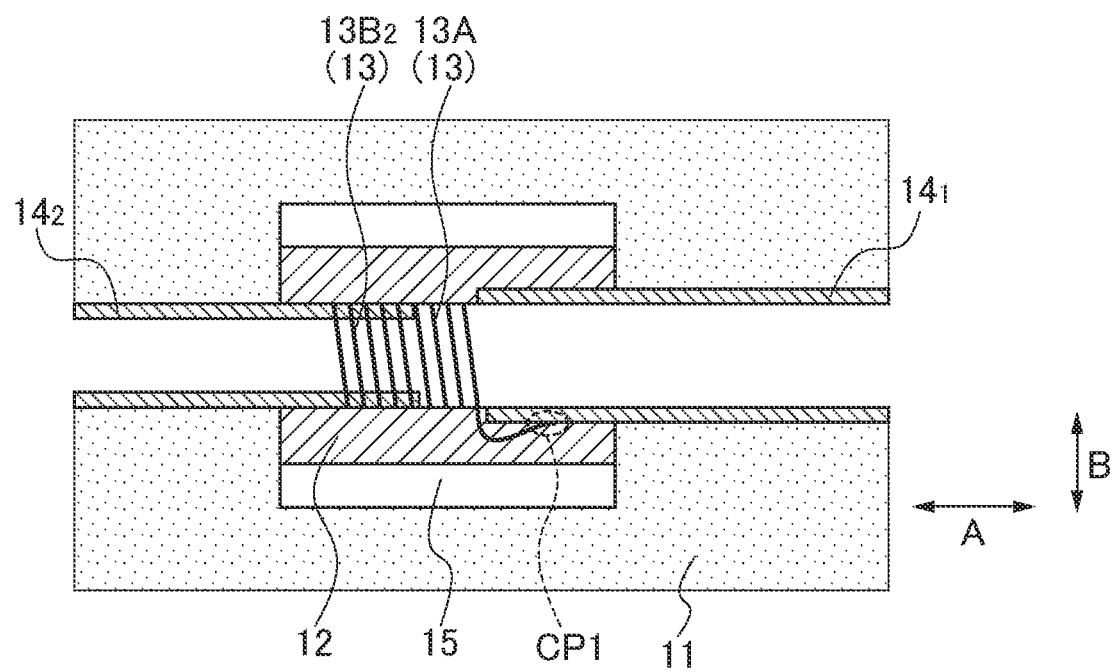
FIG. 11 is a diagram showing an atomizing unit 111 according to a modification 6.
Figure 12A:
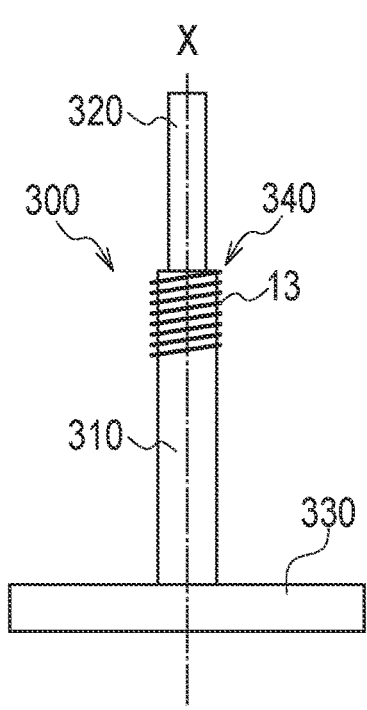
FIGS. 12 (A) to 12 (E) are diagrams for explaining a manufacturing method of an atomizing unit 111 according to a modification 7.
Figure 12B:
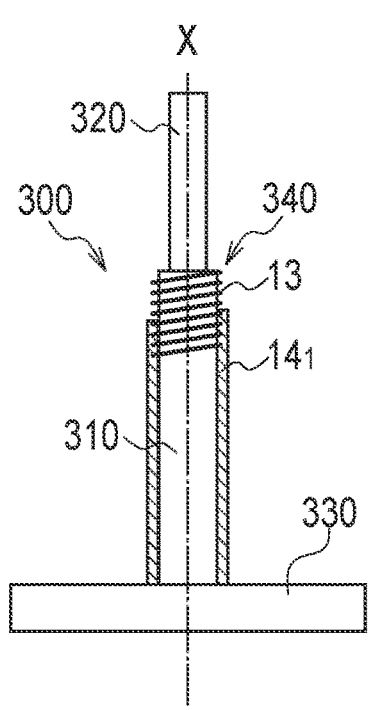
Figure 12C:
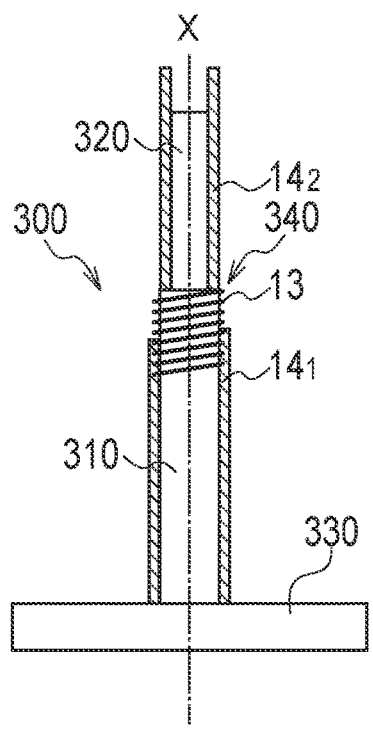
Figure 12D:
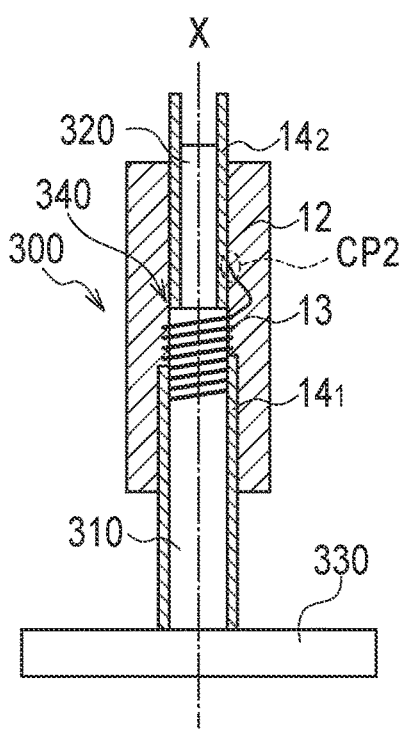
Figure 12E:
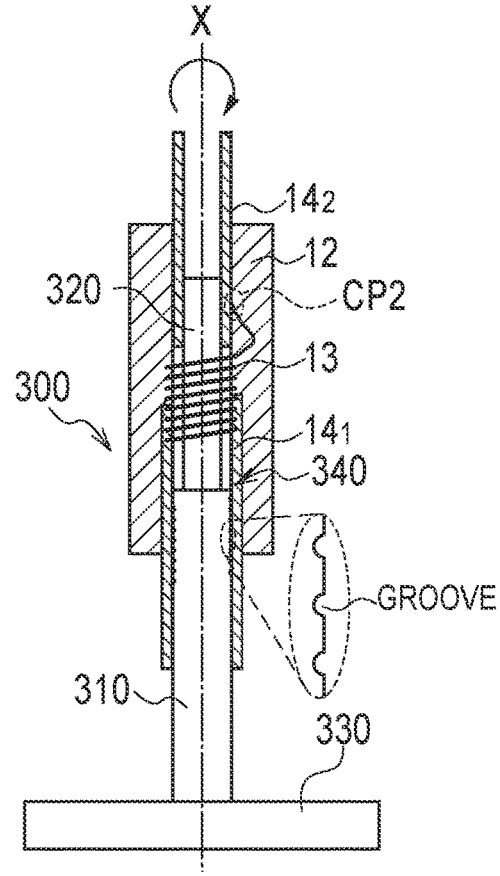
Figure 13A:
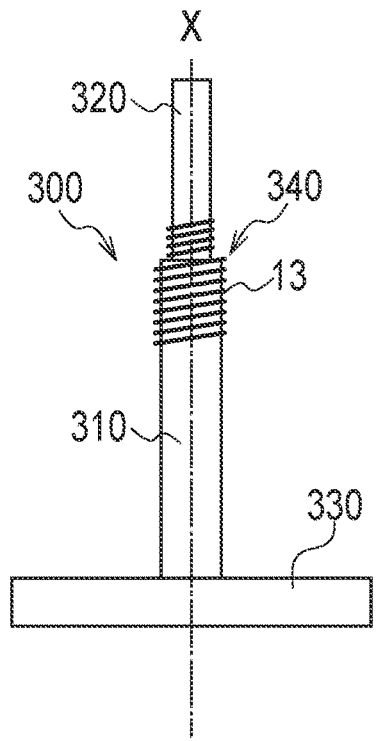
FIGS. 13 (A) to 13 (D) are diagrams for explaining a manufacturing method of an atomizing unit 111 according to a modification 8.
Figure 13B:
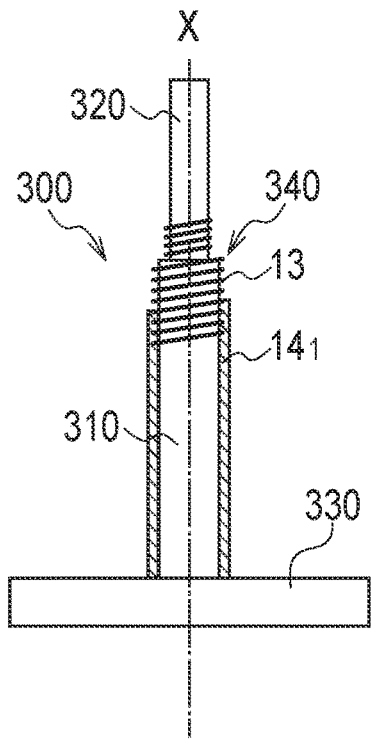
Figure 13C:
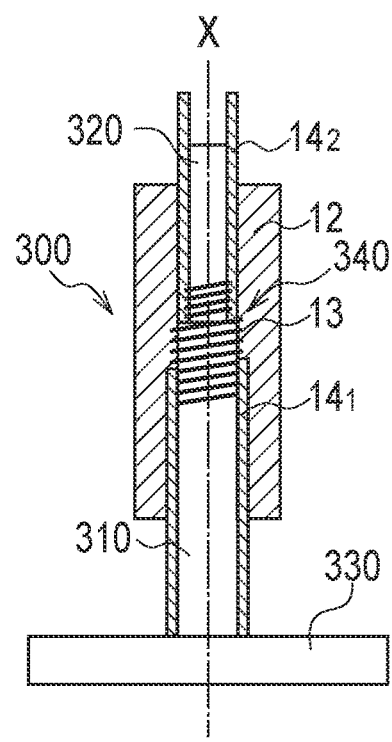
Figure 13D:
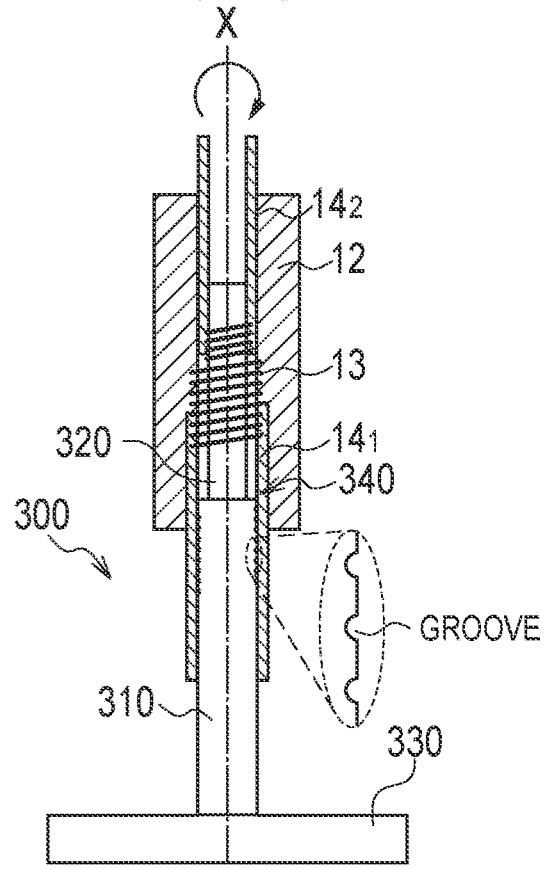
Figure 14A:
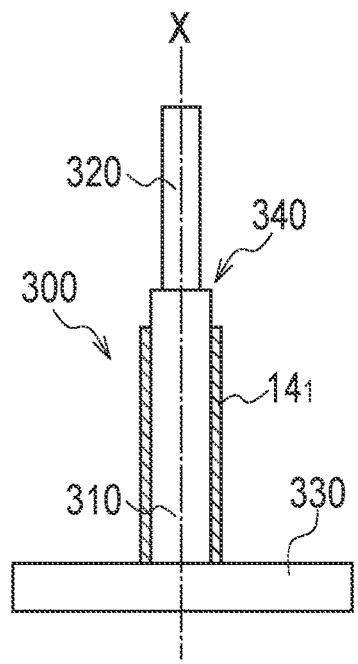
FIGS. 14 (A) to 14 (E) are diagrams for explaining a manufacturing method of an atomizing unit 111 according to a modification 9.
Figure 14B:
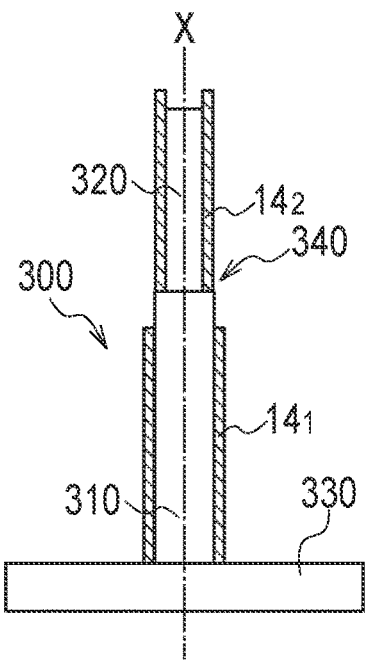
Figure 14C:
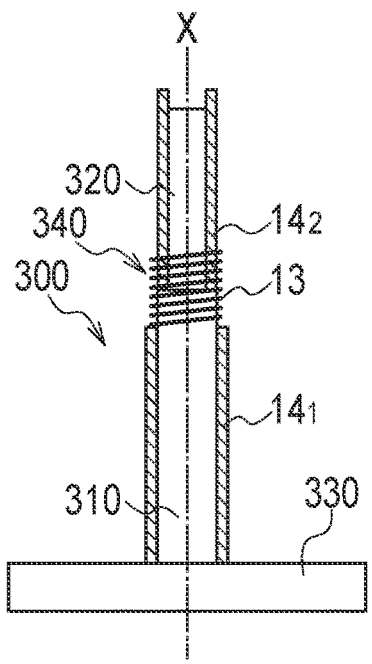
Figure 14D:
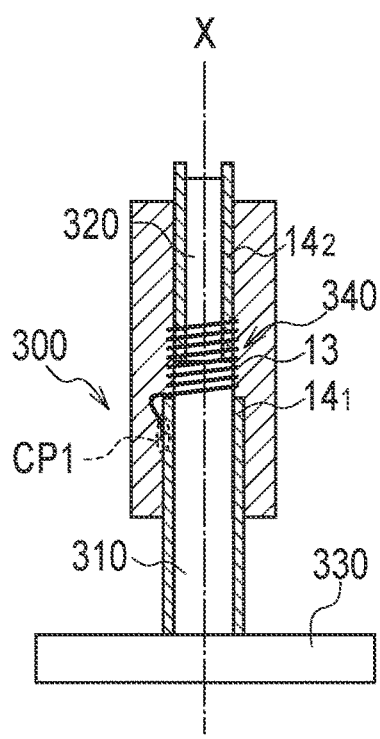
Figure 14E:
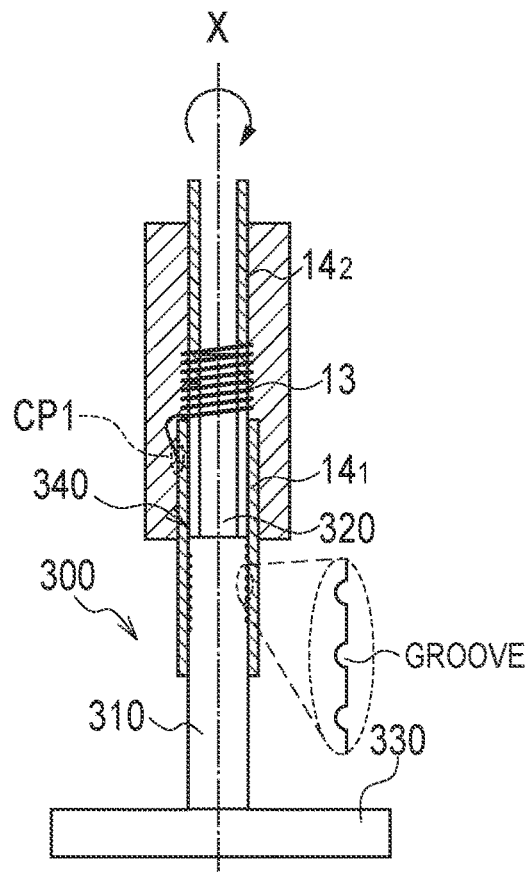

In the embodiment, the inner diameter of the cylindrical member $14_1$ is the same as the inner diameter of the cylindrical member $14_2$. In contrast, in the modified example 6, as shown in FIG. 11, the inner diameter and the outer diameter of the cylindrical member $14_1$ are larger than the inner diameter and the outer diameter of the cylindrical member $14_2$. In FIG. 11, it should be noted that the atomizing unit housing 111 X, the cap 16, the flange 17 and the like are omitted.

In such a case, as shown in FIG. 11, the heating element 13 has the heating portion 13 A and the second end portion $13\ B_2$, but does not have the first end portion $13\ B_1$. The inner side surface of the second end portion $13\ B_2$ contacts the outer side surface of the cylindrical member $14_2$. In other words, the cylindrical member $14_2$ is disposed inside the heating element 13. On the other hand, a lead wire drawn downstream from the heating portion 13 A is connected to the outer side surface or the end face of the cylindrical member $14_1$. The outer side surface or the end face of the cylindrical member $14_1$ and the lead wire constitute the first contact CP 1.

In FIG. 11, it should be noted that the lead wire is inflated for convenience of illustration, but the lead wire is actually laid between the liquid holding member 12 and the cylindrical member 14.

Operation and Effect

In the modification 6, the outer diameter of the cylindrical member $14_1$ provided on the downstream side is larger than the outer diameter of the cylindrical member $14_2$ provided on the upstream side. Therefore, as in the modification 4 and modification 5, the distance between the cover member 15 and the cylindrical member $14_1$ is smaller than the distance between the cover member 15 and the cylindrical member $14_2$, and it is possible to prevent the oversupply of the aerosol source to the liquid holding member 12 on the the downstream side.

In the modification 6, the cylindrical member $14_2$ is disposed between the liquid holding member 12 and the second end portion 13 $B_2$ in the orthogonal direction B. Therefore, since the heating element 13 is supported by the tubular member $14_2$, deformation of the heating element 13 is prevented even if the inside of the heating element 13 is hollow.

Modification 7

Hereinafter, a modification 7 of the embodiment will be described. Differences from the embodiment will mainly be described below.

In the modification 7, a method of manufacturing the atomizing unit 111 shown in the modification 4 (FIG. 9) will be described. However, since the method of attaching the atomizing unit housing 111 X, the cover member 15, the cap 16, and the flange 17 are substantially the same as those in the embodiment, their mounting methods will be omitted. In the modification 7, the base member 300 (jig) with an axis X extending along a predetermined direction has a first support portion 310 having a first outer diameter, a second support portion 320 having a second outer diameter smaller than the first outer diameter, a base portion 330, and a step portion 340. The inner diameter of the cylindrical member $14_1$ corresponds to the first outer diameter, and the inner diameter of the cylindrical member $14_2$ corresponds to the second outer diameter. The base portion 330 is a member for supporting the first support portion 310, and constitutes a first locking portion for locking the cylindrical member $14_1$. The step portion 340 is a boundary portion between the first support portion 310 and the second support portion, and constitutes a second locking portion for locking the cylindrical member $14_2$.

In the modification 7, "the inner diameter of the cylindrical member $14_1$ corresponds to the first outer diameter" means the relationship between the inner diameter of the cylindrical member $14_1$ and the outer diameter of the first support portion 310, in which the inner side surface of the cylindrical member $14_1$ is slidable along the heating element 13 disposed on the outer side surface of the first support portion 310, and the inner side surface of the cylindrical member $14_1$ contacts the heating element 13 disposed on the outer side surface of the first support portion 310. On the other hand, "the inner diameter of the cylindrical member $14_2$ corresponds to the second outer diameter" means the relationship between the inner diameter of the cylindrical member $14_2$ and the outer diameter of the second support portion 320, in which the inner side surface of the cylindrical member $14_2$ is slidable along the outer side surface of the second support portion 320, and the center axis of the cylindrical member $14_2$ does not deviate from the center axis of the second support portion 320 in a state where the cylindrical member $14_2$ is disposed on the outer side surface of the second support portion 320 (for example, a manufacturing process).

As shown in FIG. 12 (A), the heating element 13 is disposed to follow a helical groove or projection formed on the outer side surface of the first support portion 310 (step A).

Next, as shown in FIG. 12 (B), by sliding the cylindrical member $14_1$ along the axis X to a position where the cylindrical member $14_1$ is locked by the base portion 330, the cylindrical member $14_1$ is disposed along the outer side surface of the first support portion 310 (step E 1 and step E 3). The step shown in FIG. 12 (B) is a step of placing the cylindrical member $14_1$ from the side of the second support part 320 with a small outer diameter toward the side of the first support part 310 with a large outer diameter. It should be noted that in the predetermined direction along the axis X, the total length of the cylindrical member $14_1$ is shorter than the total length of the first support portion 310.

Next, as shown in FIG. 12 (C), by sliding the member $14_2$ along the axis X to a position where the cylindrical member $14_2$ is locked by the step portion 340, the cylindrical member $14_2$ is placed along the outer side surface of the second support portion 320 (step E 2 and step E 4). The step shown in FIG. 12 (C) is a step of disposing the cylindrical member $14_2$ from the side of the second support part 320 with a small outer diameter toward the side of the first support part 310 with a large outer diameter. It should be noted that the cylindrical member $14_2$ is locked by the step portion 340. Thereby, the cylindrical member $14_1$ and the cylindrical member $14_2$ are disposed in a state of being separated from each other.

Next, as shown in FIG. 12 (D), the second contact CP 2 is formed by connecting the lead wire drawn upstream from the heating portion 13 A to the outer side surface of the cylindrical member $14_2$. For example, the lead wire is fixed to the outer side surface of the cylindrical member $14_2$ by welding or soldering. The second contact CP 2 may be formed by connecting a lead wire to the end face of the cylindrical member $14_2$.

Then, by sliding the liquid holding member 12 along the axis X, the liquid holding member 12 is placed on the outer side surface of the heating element 13 and the cylindrical member 14. That is, the liquid holding member 12 is disposed to contact or come close to the heating portion 13 A of the heating element 13 (step C). Here, the step of disposing the liquid holding member 12 to contact or come close to the heating portion 13 A of the heating element 13 is a step of disposing the liquid holding member 12 from the side of the second support portion 320 with a small outer diameter to the side of the first support portion 310 with a large outer diameter.

Next, in FIG. 12 (E), the base member 300 (jig) is rotated about the axis X as a rotation axis to separate the whole heating element 13 from the groove or projection of the base member 300 (step B). The aerosol intake and the air flow path are formed in the step shown in FIG. 12 (E). This is the same as in the embodiment.

Although omitted in FIG. 12, as in the embodiment, the cylindrical member 14 is preferably fixed to the atomizing unit housing 111 X (the housing cap body 111 $X_1$ and the housing cylindrical body 111 $X_2$) via the cap 16, the flange 17, and the like. That is, it is preferable that the step shown in FIG. 12 (E) is performed after fixing the cylindrical member 14 to the atomizing unit housing 111 X.

In FIG. 12, the lead wire is inflated for convenience of illustration, but it should be noted that the lead wire is actually laid between the liquid holding member 12 and the cylindrical member 14.

Operation and Effect

In the modification 7, the second contact CP 2 is formed by connecting the lead wire drawn upstream from the heating portion 13 A to the outer side surface or the end face of the cylindrical member $14_2$. Therefore, it is easy to form the second contact CP 2.

In the modification 7, the cylindrical member $14_1$ is locked by the base portion 330, and the cylindrical member $14_2$ is locked by the step portion 340. Therefore, it is easy to position the cylindrical member $14_1$ and the cylindrical member $14_2$, and it is easy to separate the cylindrical member $14_1$ and the cylindrical member $14_2$ from each other by a distance corresponding to the heating portion 13 A.

In the modification 7, the cylindrical member $14_1$, the cylindrical member $14_2$, and the liquid holding member 12 are slid from the side of the second support portion 320 with a small outer diameter toward the side of the first support portion 310 with a large outer diameter. Therefore, it is easy to slide these members.

Modification 8

Hereinafter, a modification 8 of the embodiment will be described. Differences from the modification 7 will mainly be described below.

In the modification 8, a method of manufacturing the atomizing unit 111 shown in the modification 5 (FIG. 10) will be described. However, since the method of attaching the atomizing unit housing 111 X, the cover member 15, the cap 16, and the flange 17 are substantially the same as those in the embodiment, their mounting methods will be omitted. In the modification 8, the same base member 300 (jig) as in the modification 7 is used.

In the modification 8, "the inner diameter of the cylindrical member $14_1$ corresponds to the first outer diameter" means the relationship between the inner diameter of the cylindrical member $14_1$ and the outer diameter of the first support portion 310, in which the inner side surface of the cylindrical member $14_1$ is slidable along the heating element 13 disposed on the outer side surface of the first support portion 310, and the inner side surface of the cylindrical member $14_1$ contacts the heating element 13 disposed on the outer side surface of the first support portion 310. Similarly, "the inner diameter of the cylindrical member $14_2$ corresponds to the second outer diameter" means the relationship between the inner diameter of the cylindrical member $14_2$ and the outer diameter of the second support portion 320, in which the cylindrical member $14_2$ is slidable along the heating element 13 disposed on the outer side surface of the second support portion 320, and the heating element 13 disposed in the second support portion 320 contacts the inner side surface of the cylindrical member $14_2$.

As shown in FIG. 13 (A), the heating element 13 is disposed to follow a helical groove or projection formed on the outer side surface of the first support portion 310 and the outer side surface of the second support portion 320 (step A).

Next, as shown in FIG. 13 (B), by sliding the cylindrical member $14_1$ along the axis X to the position where the cylindrical member $14_1$ is locked by the base portion 330, the cylindrical member $14_1$ is disposed along the outer side surface of the first support portion 310 (step E 1 and step E 3).

Next, as shown in FIG. 13 (C), by sliding the cylindrical member $14_2$ along the axis X to a position where the cylindrical member $14_2$ is locked by the step portion 340, the cylindrical member $14_2$ is disposed along the outer side surface of the second support portion 320 (step E 2 and step E 4). Then, by sliding the liquid holding member 12 along the axis X, the liquid holding member 12 is disposed on the outer side surface of the heating element 13 and the cylindrical member 14.

Next, in FIG. 13 (D), the base member 300 (jig) is rotated about the axis X as a rotation axis to separate the whole heating elements 13 from the groove or projection of the base member 300 (step B). The aerosol intake and the air flow path are formed in the step shown in FIG. 13 (D). This is the same as in the embodiment.

Operation and Effect

In the modification 8, the cylindrical member $14_1$ is locked by the base portion 330, and the cylindrical member $14_2$ is locked by the step portion 340. Therefore, it is easy to position the cylindrical member $14_1$ and the cylindrical member $14_2$, and it is easy to separate the cylindrical member $14i$ and the cylindrical member $14_2$ from each other by a distance corresponding to the heating portion 13 A.

In the modification 8, the cylindrical member $14i$, the cylindrical member $14_2$, and the liquid holding member 12 are slid from the side of the second support portion 320 with a small outer diameter toward the side of the first support portion 310 with a large outer diameter. Therefore, it is easy to slide these members.

Modification 9

Hereinafter, a modification 9 of the embodiment will be described. Differences from the modification 7 will mainly be described below.

In the modification 9, a method of manufacturing the atomizing unit 111 shown in the modification 6 (FIG. 11) will be described. However, since the method of attaching the atomizing unit housing 111 X, the cover member 15, the cap 16, and the flange 17 are substantially the same as those in the embodiment, their mounting methods will be omitted. In the modification 9, the same base member 300 (jig) as in the modification 7 is used.

In the modification 9, "the inner diameter of the cylindrical member $14_1$ corresponds to the first outer diameter" means the relationship between the inner diameter of the cylindrical member $14_1$ and the outer diameter of the first support portion 310, in which the inner side surface of the cylindrical member $14_1$ is slidable along the heating element 13 disposed on the outer side surface of the first support portion 310, and the center axis of the cylindrical member $14_1$ does not deviate from the center axis of the first support portion 310 in a state where the cylindrical member $14_1$ is disposed on the outer side surface of the first support portion 310 (for example, a manufacturing process). Similarly, "the inner diameter of the cylindrical member $14_2$ corresponds to the second outer diameter" means the relationship between the inner diameter of the cylindrical member $14_2$ and the outer diameter of the second support portion 320, in which the cylindrical member $14_2$ is slidable along the outer side surface of the second support portion 320, and the center axis of the cylindrical member $14_2$ does not deviate from the center axis of the second support portion 320 in a state where the cylindrical member $14_2$ is disposed on the outer side surface of the second support portion 320 (for example, a manufacturing process).

As shown in FIG. 14 (A), by sliding the cylindrical member $14_1$ along the axis X to a position where the cylindrical member $14_1$ is locked by the base portion 330, the cylindrical member $14_1$ is disposed along the outer side surface of the first support portion 310 (step E 1 and step E 3).

As shown in FIG. 14 (B), by sliding the cylindrical member $14_2$ along the axis X to a position where the cylindrical member 1421 is locked by the step portion 340, the cylindrical member $14_2$ is disposed along the outer side surface of the second support portion 320 (step E 2 and step E 4).

Here, after sliding the cylindrical member $14_2$ along the outer side surface of the second support portion 320, the outer side surface of the cylindrical member $14_2$ preferably does not have a step with the outer side surface of the first support portion 310. In other words, the outer diameter of the cylindrical member $14_2$ is preferably equal to the outer diameter of the first support portion 310.

Next, as shown in FIG. 14 (C), the heating element 13 is disposed on the outer side surface of the first support portion 310 and the outer side surface of the cylindrical member $14_2$ (step A). Here, a helical groove or projection is provided on the outer side surface of the first support portion 310.

Furthermore, it is preferable that a helical groove or projection is also provided on the outer side surface of the cylindrical member $14_2$. It is preferable that the helical groove or projection formed on the outer side surface of the cylindrical member $14_2$ is continuous with a groove or a projection having a spiral shape and formed on the outer side surface of the first support portion 310. The step A is a step of disposing the heating element 13 to be along the groove or the projection having the spiral shape and formed on the outer side surface of the first support portion 310 and the outer side surface of the cylindrical member $14_2$.

Next, as shown in FIG. 14 (D), the first contact CP 1 is formed by connecting the lead wire drawn downstream from the heating portion 13 A to the outer side surface of the cylindrical member $14_1$. For example, the lead wires are fixed to the outer side surface of the cylindrical member $14_1$ by welding or soldering. The first contact CP 1 may be formed by connecting a lead wire to the end face of the cylindrical member $14_1$.

Then, by sliding the liquid holding member 12 along the axis X, the liquid holding member 12 is disposed on the outer side surface of the heating element 13 and the cylindrical member 14. That is, the liquid holding member 12 is disposed to contact or come close to the heating portion 13 A of the heating element 13 (step C).

Next, in FIG. 14 (E), the base member 300 (jig) is rotated about the axis X as a rotation axis to separate the whole heating element 13 from the groove or projection of the base member 300 (step B). The aerosol intake and the air flow path are formed in the step shown in FIG. 14 (E). This is the same as in the embodiment.

In FIG. 14, the lead wire is inflated for convenience of illustration, but it should be noted that the lead wire is actually laid between the liquid holding member 12 and the cylindrical member 14.

Operation and Effect

In the modification 9, the first contact CP 1 is formed by connecting the lead wire drawn downstream from the heating portion 13 A to the outer side surface or the end face of the cylindrical member $14_1$. Therefore, it is easy to form the first contact CP 1.

In the modification 9, the cylindrical member $14_1$ is locked by the base portion 330, and the cylindrical member $14_2$ is locked by the step portion 340. Therefore, it is easy to position the cylindrical member $14_1$ and the cylindrical member $14_2$, and it is easy to separate the cylindrical member $14_1$ and the cylindrical member $14_2$ from each other by a distance corresponding to the heating portion 13 A.

In the modification 9, the cylindrical member $14_1$, the cylindrical member $14_2$, and the liquid holding member 12 are slid from the side of the second support portion 320 with a small outer diameter toward the side of the first support portion 310 with a large outer diameter. Therefore, it is easy to slide these members.

In the modification 9, it is preferable to dispose the heating element 13 to be along the groove or the projection having the spiral shape and formed on the outer side surface of the first support portion 310 and the outer side surface of the cylindrical member $14_2$. With such a configuration, it is difficult to form a step between the outer side surface of the cylindrical member $14_2$ and the outer side surface of the first support portion 310, and it is easy to dispose the heating element 13. Further, since the heating element 13 (the second end portion 13 $B_2$) is disposed on the outer side surface of the cylindrical member $14_2$, it is easy to fix the cylindrical member $14_2$ and the heating element 13 (the second end portion 13 $B_2$).

Modification 10

Hereinafter, a modification 10 of the embodiment will be described. Differences from the embodiment will mainly be described below.

Figure 15:
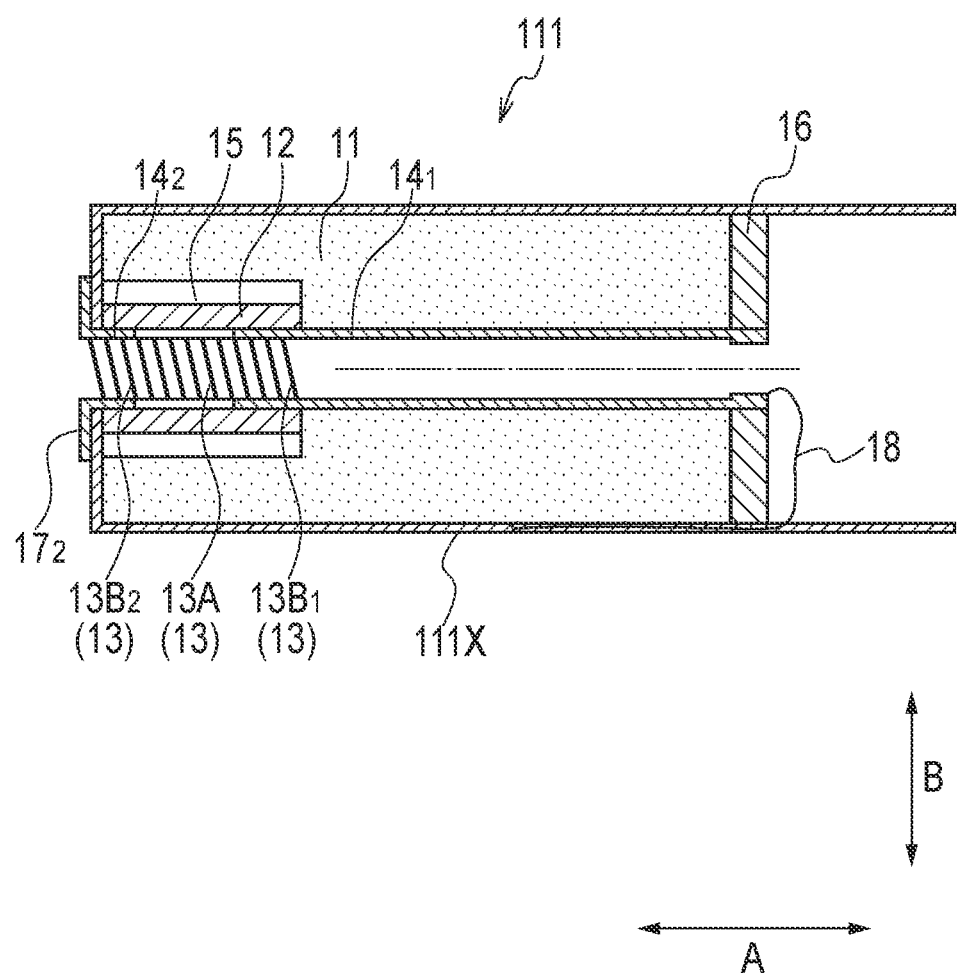
FIG. 15 is a diagram showing an atomizing unit 111 according to a modification 10.

In the embodiment, the flange $17_1$ is disposed on the downstream end face of the cap 16. In contrast, in the modification 10, as shown in FIG. 15, the flange $17_1$ is not particularly provided, and the lead wire 18 extending from the first pole of the power source is connected to the inner side surface of the cylindrical member $14_1$. The lead wire 18 may be guided to the cylindrical member $14_1$ through the inside of the atomizing unit housing 111 X.

In the modification 10, the lead wire 18 is provided downstream of the cap 16 in a separating direction that separates the cap 16 from the reservoir 11. In other words, when attempting to separate the cap 16 from the reservoir 11, the lead wire 18 is caught by the cap 16. Therefore, since the lead wire 18 is pulled by the cap 16, deformation of the heating element 13 occurs due to detachment of the lead wire 18 from the cylindrical member $14_1$, disconnection of the lead wire 18, or the pulling of the cylindrical member $14_1$ by the lead wire 18.

Further, the cap 16 is fixed or fitted to the cylindrical member $14_1$. Therefore, when attempting to separate the cap 16 from the reservoir 11, deformation of the heating element 13 occurs due to the pulling of the cylindrical member $14_1$.

Operation and Effect

In the modification 10, the lead wire 18 is provided downstream of the cap 16 in the separating direction that separates the cap 16 from the reservoir 11. Therefore, when attempting to separate the cap 16 from the reservoir 11, since the heating element 13 and the power supply member are broken, it is possible to effectively decrease the use of the flavor inhaler 100 accompanied by reinjection of the aerosol source to the reservoir 11.

Modification 11

Hereinafter, a modification 11 of the embodiment will be described below. Differences from the embodiment will mainly be described below.

Figure 16:
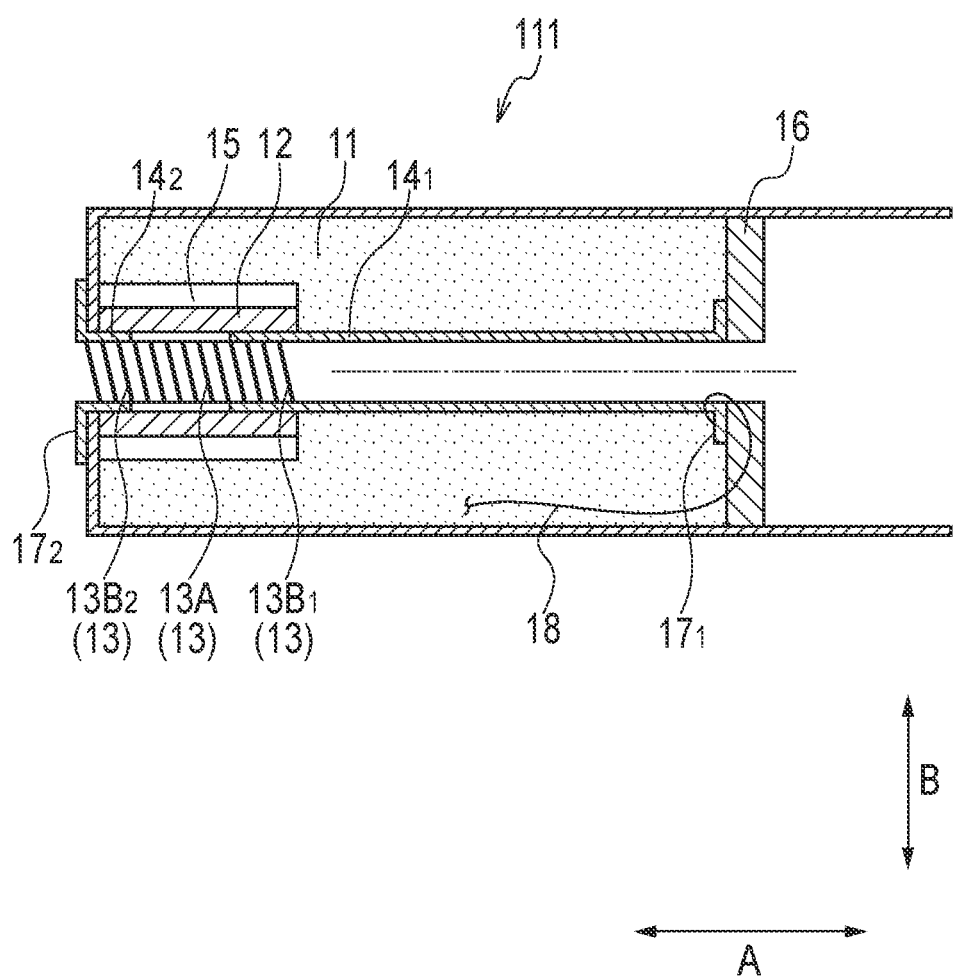
FIG. 16 is a diagram showing an atomizing unit 111 according to a modification 11.

In the embodiment, the flange $17_1$ is disposed on the downstream end face of the cap 16. In contrast, in the modification 11, the flange $17_1$ is disposed on the upstream end face of the cap 16, as shown in FIG. 16. Here, a lead wire 18 extending from the first pole of the power source is connected to the flange $17_1$. The lead wire 18 may be guided to the flange $17_1$ through the inside of the cap 16.

Operation and Effect

In the modification 11, the lead wires 18 is arranged to pass through the interior of the cap 16 in the same manner as in the modification 10. Therefore, when attempting to separate the cap 16 from the reservoir 11, since the heating element 13 and the power supply member are broken, it is possible to effectively decrease the use of the flavor inhaler 100 accompanied by reinjection of the aerosol source to the reservoir 11.

Modification 12

Hereinafter, a modification 12 of the embodiment will be described. Differences from the embodiment will mainly be described below. In the modification 12, it should be noted that except for the atomizing unit 111, the configuration of the flavor inhaler 100 is similar to that of the embodiment.

In the embodiment, the inlet 112 A is provided in the electrical component unit housing 112 X, the liquid holding member 12 is disposed on the outer side surface of the cylindrical member 14, and the cylindrical member 14 forms an air flow path. On the other hand, in the modification 12, the inlet 112 A is provided in the atomizing unit housing 111 X, the liquid holding member 12 is disposed inside the cylindrical member 14, and the air flow path is formed outside the cylindrical member 14.

Figure 17:
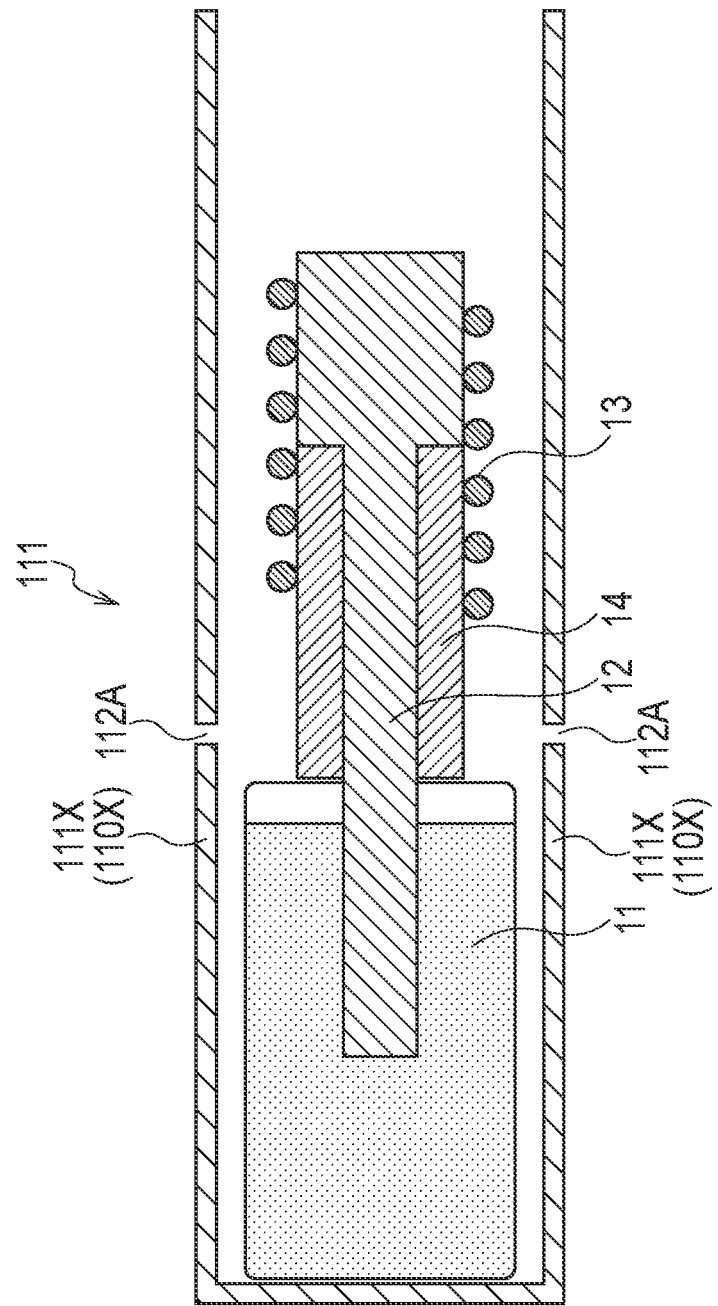
FIG. 17 is a diagram showing an atomizing unit 111 according to a modification 12.

Specifically, as shown in FIG. 17, the atomizing unit 111 includes a reservoir 11, a liquid holding member 12, a heating element 13, and a cylindrical member 14. Specifically, as shown in FIG. 17, the atomizing unit 111 includes a reservoir 11, a liquid holding member 12, a heating element 13, and a cylindrical member 14. The reservoir 11, the liquid holding member 12, the heating element 13, and the cylindrical member 14 are housed in the atomizing unit housing 111 X having the inlet 112 A. The liquid holding member 12 has an insertion portion inserted in the cylindrical member 14 and an exposed portion exposed from the cylindrical member 14. The insertion portion contacts the aerosol source stored in the reservoir 11. The exposed portion inflates in the orthogonal direction B than the insertion portion.

The heating element 13 is disposed over the outer side surface of the cylindrical member 14 and the outer side surface of the exposed portion of the liquid holding member 12. The heating element 13 is disposed to contact or come close to the exposed portion of the liquid holding member 12.

In the modification 12, the air introduced from the inlet 112 A is guided to the downstream side through the outer side surface of the exposed portion of the cylindrical member 14 and the liquid holding member 12, and the aerosol atomized by the heating element 13 is delivery to the downstream side. In the modification 12, the cylindrical member 14 is not formed of a conductive member, and the heating element 13 is connected to a power source by a power supply member such as a lead wire.

Modification 13

Hereinafter, a modification 13 of the embodiment will be described. Differences from the embodiment will mainly be described below.

Figure 18A:
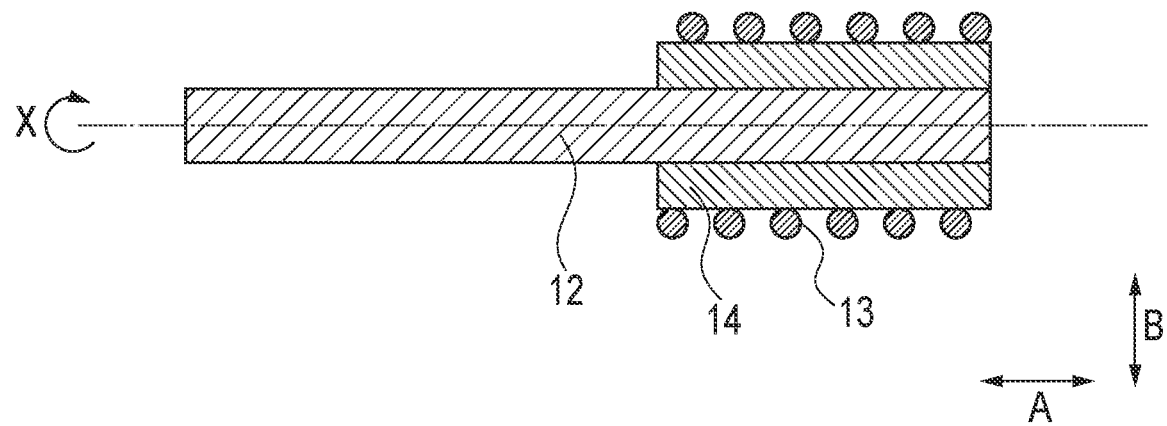
FIGS. 18 (A) and 18 (B) are diagrams for explaining a manufacturing method of an atomizing unit 111 according to a modification 13.
Figure 18B:
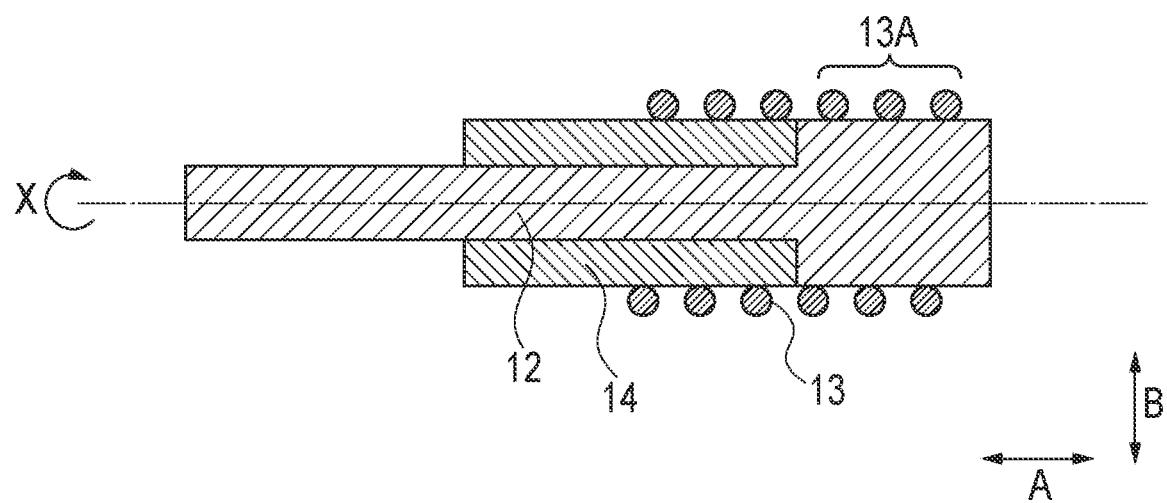

In the modification 13, the manufacturing method of the atomizing unit 111 described in the modification 12 will be described. FIG. 18 is a diagram for explaining a method of manufacturing the atomizing unit 111 according to the modification 13. In FIG. 18, it should be noted that the atomizing unit housing 111 X, the cap 16, the flange 17, and the like are omitted.

Specifically, as shown in FIG. 18 (A), a heating element 13 is formed to follow a helical groove or projection formed on the outer side surface of the cylindrical member 14 having an axis X extending along a predetermined direction A (step A). Further, the cylindrical member 14 and the heating element 13 are electrically connected (step D). It should be noted here that the liquid holding member 12 is disposed inside the cylindrical member 14 in the orthogonal direction B.

Next, in FIG. 18 (B), the cylindrical member 14 is rotated about the axis X as a rotation axis, and a part of the heating element 13 is separated from the groove or the projection of the cylindrical member 14 (step B).

In the modification 13, by separating a part of the heating element 13 from the groove or the projection of the cylindrical member 14, restriction of expansion of the liquid holding member 12 in the outward direction is released, and the liquid holding member 12 is disposed to contact or come close to the heating element 13 (step C).

In other words, in the step shown in FIG. 18 (B), a part of the heating element 13 is separated from the cylindrical member 14 by the rotation of the cylindrical member 14, a part of the liquid holding member 12 disposed inside the cylindrical member 14 is separated from the cylindrical member 14, and a part of the liquid holding member 12 is brought into contact with or close to a part of the heating element 13 by expansion of a part of the liquid holding member 12 (step B and step C). In the case where a part of the holding member 12 is brought into contact with a part of the heating element 13, the step shown in FIG. 18 B is a step of disposing the liquid holding member 12 while the liquid holding member 12 presses the inner side surface of a part (heating portion 13 A) of the heating element 13. Further, the step shown in FIG. 18 (B) is a step of disposing the liquid holding member 12 to contact the entire circumference of the inner side surface of a part (heating portion 13 A) of the heating element 13.

Here, when a part of the heating element 13 is separated from the groove or projection of the cylindrical member 14, it should be noted that at least the liquid holding member 12 is preferably fixed to prevent the liquid holding member 12 from moving along the predetermined direction A accompanied by the rotation of the cylindrical member 14. A counterpart to which the liquid holding member 12 is fixed may be any one that does not move along with the rotation of the cylindrical member 14.

In the case of fixing the heating element 13 to the cylindrical member 14, such a fixing step is performed after a part of the heating element 13 is separated from the groove or the projection of the cylindrical member 14.

In the modification 13, a part of the heating element 13 is separated from the groove or the projection of the cylindrical member 14 in a state where the liquid holding member 12 is disposed inside the cylindrical member 14. However, the liquid holding member 12 may be disposed to contact or come close to the heating element 13 after separating a part of the heating element 13 from the groove or the projection of the cylindrical member 14. For example, in a state where a part of the heating element 13 is separated from the groove or the projection of the cylindrical member 14, the exposed portion of the liquid holding member 12 may contact or come close to the heating element 13 by pushing the liquid holding member 12 into the cylindrical member 14 from the side where the heating element 13 is not provided to the side where the heating element 13 is provided.

Modification 14

Hereinafter, a modification 14 of the embodiment will be described. Differences from the embodiment will mainly be described below.

In the embodiment, the base member 300, which is a jig having a cylindrical shape, is not included in the atomizing unit 111 as a part of the atomizing unit 111. However, in the modification 14, the base member 300 is included in the atomizing unit 111 as a part of the atomizing unit 111.

Figure 19:
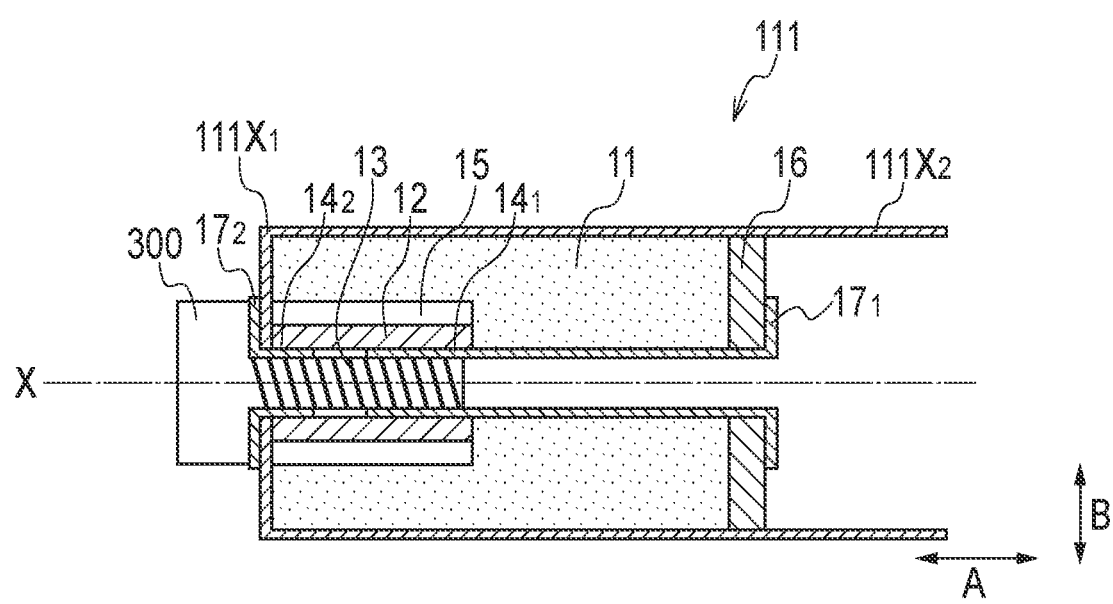
FIG. 19 is a diagram showing an atomizing unit 111 according to a modification 14.

That is, in the modification 14, the atomizing unit 111 is, as shown in FIG. 19, is disposed to contact or come close to the base member 300 having an axis extending along a predetermined direction A, the heating element 13 disposed to be along the helical groove or projection formed on the side surface of the base member 300, and at least a part of the heating element 13. The atomizing unit 111 includes at least the liquid holding member 12 holding an aerosol source, and the atomizing unit housing 111 X accommodating the heating element 13 and the liquid holding member 12. At least a part of the base member 300 is preferably exposed from the atomizing unit housing 111 X. However, the atomizing unit 111 may include other parts (for example, the reservoir 11, the cylindrical member 14, the cover member 15, the cap 16, the flange 17, etc.) as in the embodiment.

The method of manufacturing the atomizing unit 111 according to the modification 14 includes a step (step F) of housing the heating element 13 and the liquid holding member 12 in the atomizing unit housing 111 X in a state where a part of the base member 300 is exposed from the atomizing unit housing 111 X, instead of a step (step B) of rotating the base member 300 about the axis X as a rotation axis to separate the heating element 13 from the groove or the projection. The step of separating the heating element 13 from the groove or the projection is performed, for example, when the user who acquired the atomizing unit 111 uses the atomizing unit 111.

In FIG. 19, as in the embodiment (for example, FIGS. 4 and 5) and the like, the case where the base member 300 is a jig is exemplified. However, the modification 14 is not limited to the example shown in FIG. 19. The base member 300 may be the cylindrical member 14 (the cylindrical member $14_1$ and the cylindrical member $14_2$) as shown in FIG. 7 (A) of the modification 2 or FIG. 8 (A) of the modification 3. In such a case, the liquid holding member 12 is disposed to be in contact with or close to at least a part of the heating element 13 by rotating the cylindrical member 14 about the axis X as a rotation axis to separate the heating element 13 from the groove or the projection. In the atomizing unit 111 with such a configuration, it is preferable that a part of the cylindrical member 14 is exposed from the atomizing unit housing 111 X.

Operation and Effect

In the modification 14, since the base member 300 is separated from the heating element 13 at the time of use by the user, the state where the heating element 13 is held by the base member 300 is maintained until the user uses the atomizing unit 111. Therefore, deformation of the heating element 13 is prevented until the user uses the atomizing unit 111. Further, since the base member 300 fulfills the function of the lid, leakage of the aerosol source is prevented until the user uses the atomizing unit 111. Furthermore, it is possible to clearly grasp before and after use of the atomizing unit 111.

In the modification 14, it is preferable that at least a part of the base member 300 is exposed from the atomizing unit housing 111 X. With such a configuration, it is easy to separate the heating element 13 from the groove or the projection by the rotation of the base member 300 before using the atomizing unit 111.

In the modification 14, the step of housing the heating element 13 and the liquid holding member 12 in the atomizing unit housing 111 X is preferably performed in a state in which a part of the base member 300 is exposed from the atomizing unit housing 111 X. By such a method, it becomes easy to separate the heating element 13 from the groove or the projection by the rotation of the base member 300 before using the atomizing unit 111.

OTHER EMBODIMENTS

Although the present invention has been described with reference to the above-described embodiments, it should not be understood that the description and drawings constituting a part of this disclosure limit the present invention. From this disclosure, various alternative embodiments, examples and operational techniques will be apparent to those skilled in the art.

In the embodiment, the reservoir 11 is disposed outside the liquid holding member 12 in the orthogonal direction B. However, the embodiment is not limited to this. The reservoir 11 may be in contact with the liquid holding member 12 and may not be disposed outside the liquid holding member 12 in the orthogonal direction B. In a state in which the reservoir 11 is not disposed outside the liquid holding member 12 in the orthogonal direction B, the cover member 15 can prevent the aerosol source unexpectedly leaked from the reservoir 11 from being supplied from the outer peripheral surface of the liquid holding member 12 to the liquid holding member 12, before the flavor inhaler 100 is used or while the flavor inhaler 100 is used.

In the embodiment, the liquid holding member 12 has a cylindrical shape. However, the embodiment is not limited to this. The liquid holding member 12 may have a string shape.

In the embodiment, the members such as the liquid holding member 12 and the cover member 15 have a cylindrical shape and are disposed outside the heating element 13 by sliding along the predetermined direction A. However, the embodiment is not limited to this. The members such as the liquid holding member 12 and the cover member 15 may have a sheet shape and may be wound around the heating element 13.

In the embodiment, the supply port for supplying the aerosol source to the reservoir 11 is provided at the downstream end of the reservoir 11, and the cap 16 closes the downstream end of the reservoir 11. However, the embodiment is not limited to this. The supply port is provided at the upstream end of the reservoir 11 (the end of the reservoir 11 at the upstream of the air flow path), and the cap 16 may close the upstream end of the reservoir 11.

In the embodiment, the heating element 13 is formed of a wire having a spiral shape, and is a coil having a shape extending along the predetermined direction A, and the inside of the heating element 13 is hollow. However, the embodiment is not limited to this. The inside of the heating element 13 may be solid. For example, as described in the modification 12 and modification 13, the liquid holding member 12 may be provided inside the heating element 13.

In the embodiment, the heating element 13 is formed of a wire having a spiral shape. However, the embodiment is not limited to this. The heating element 13 may be formed of a conductive member having another shape.

In the embodiment, the case where the cylindrical member 14 forming at least a part of the air flow path is formed of a conductive member has been exemplified. However, the embodiment is not limited to this. The cylindrical member 14 may be formed of a member other than a conductive member.

In the embodiment, a lead wire 18 is provided as a member for connecting the power source and the cylindrical member 14. However, the embodiment is not limited to this. For example, a member for connecting the power source and the cylindrical member 14 may form an electrical path, and may be a part of a housing or the like constituting the flavor inhaler 100.

In the modifications 4 to 6 and 7 to 9, the outer diameter of the cylindrical member $14_1$ is larger than the outer diameter of the cylindrical member $14_2$. However, the embodiment is not limited to this. For example, in the modifications 4, 5, 7, and 8, the outer diameter of the cylindrical member $14_1$ may be equal to the outer diameter of the cylindrical member $14_2$. For example, when the inner diameter of the cylindrical member $14_1$ is larger than the inner diameter of the cylindrical member $14_2$ and the outer diameter of the cylindrical member $14_1$ is equal to the outer diameter of the cylindrical member $14_2$, it should be noted that the thickness of the cylindrical member $14_2$ is larger than the thickness of the cylindrical member $14_1$.

Although not specifically mentioned in the embodiment, the fixing method of each member may be adhesion or welding.

Although not specifically mentioned in the embodiment, the liquid holding member 12 may be formed of, for example, a sponge-like elastic member, and may expand and may contact or come close to the heating element 13 when the slide member 400 and the cylindrical member 14 which have compressed the liquid holding member 12 are removed.

In the embodiment, the heating element 13 is illustrated as an atomizing portion for atomizing the aerosol source. However, the embodiment is not limited to this. The atomizing portion may have a configuration that the aerosol source is atomized by the power supply output supplied to the atomizing portion, and for example, may atomize the aerosol source by ultrasonic vibration.

The invention claimed is:

1. An atomizing unit comprising:
   a reservoir configured to store an aerosol source;
   an atomizing portion configured to atomize the aerosol source; and
   a cap configured to cover a supply port for supplying the aerosol source to the reservoir,
   wherein at least one of the atomizing portion and a power supply member electrically connected to a power source and the atomizing portion is configured to be broken by a movement of separating the cap from the reservoir,
   wherein the atomizing unit comprises the supply port, and
   wherein the supply port is provided on the opposite side of a connection part to the power source with respect to the reservoir.

2. The atomizing unit according to claim 1, wherein the connection part connecting the power source, the reservoir, the cap and a mouthpiece side opening are arranged side by side in this order in a predetermined direction in which aerosol atomized by the atomizing portion is directed toward the mouthpiece-side opening.

3. The atomizing unit according to claim 2, wherein the connection part to the power source, the reservoir, the cap, and the mouthpiece side opening are arranged on a straight line.

4. The atomizing unit according to claim 1, wherein the supply port is open toward a predetermined direction in which the aerosol atomized by the atomizing portion is directed toward the mouthpiece side opening, and the cap is disposed to cover the supply port from the mouthpiece side opening.

5. The atomizing unit according to claim 1, wherein the supply port is provided at an end of the reservoir on a downstream side of an air flow path.

6. The atomizing unit according to claim 1, wherein the atomizing portion is deformed along with a movement of separating the cap from the reservoir.

7. The atomizing unit according to claim 1, wherein the power supply member protrudes toward an opposite side of the reservoir in a direction perpendicular to the face of the cap.

8. The atomizing unit according to claim 1, wherein the power supply member includes:
   a first power supply portion including a part extending from the atomizing portion to the connection part to the power source; and
   a second power supply portion extending from the atomizing portion to the opposite side of the connection part to the power source.

9. The atomizing unit according to claim 1, wherein the power supply member is disposed through the inside of the cap.

10. The atomizing unit according to claim 1, wherein the power supply member is fixed to the cap.

11. The atomizing unit according to claim 1, comprising:
    a cylindrical member having a tubular shape forming at least a part of an air flow path and formed of a conductive member,
    wherein the power supply member includes the cylindrical member.

12. The atomizing unit according to claim 1, wherein the atomizing portion is more likely to break than the power supply member.

13. The atomizing unit according to claim 1, wherein the atomizing portion is a coil having a shape extending along a predetermined direction in which aerosol atomized by the atomizing portion is directed toward the mouthpiece side opening.

14. The atomizing unit according to claim 13, wherein an inside of the coil is hollow.

15. An atomizing unit comprising:
a reservoir configured to store an aerosol source;
an atomizing portion configured to atomize the aerosol source; and
a cap configured to cover a supply port for supplying the aerosol source to the reservoir,
wherein at least one of the atomizing portion and a power supply member electrically connected to a power source and the atomizing portion is configured to be broken by a movement of separating the cap from the reservoir, and
the supply port is provided at an end of the reservoir on a downstream side of an air flow path.

* * * * *